(12) United States Patent
Saunders et al.

(10) Patent No.: US 11,918,344 B2
(45) Date of Patent: Mar. 5, 2024

(54) METHODS AND APPARATUSES FOR ANALYZING ONE OR MORE ANALYTES FROM A USER

(71) Applicant: ResMed Inc., San Diego, CA (US)

(72) Inventors: Francis Eric Saunders, San Diego, CA (US); Jose Ricardo Dos Santos, San Diego, CA (US)

(73) Assignee: ResMed Inc., San Diego, CA (US)

( * ) Notice: Subject to any disclaimer, the term of this patent is extended or adjusted under 35 U.S.C. 154(b) by 0 days.

(21) Appl. No.: 17/301,415

(22) Filed: Apr. 1, 2021

(65) Prior Publication Data

US 2021/0219867 A1    Jul. 22, 2021

Related U.S. Application Data

(63) Continuation of application No. PCT/US2020/025905, filed on Mar. 31, 2020.

(60) Provisional application No. 62/902,748, filed on Sep. 19, 2019, provisional application No. 62/863,095, filed on Jun. 18, 2019, provisional application No. 62/827,102, filed on Mar. 31, 2019.

(51) Int. Cl.
| | |
|---|---|
| *A61B 5/08* | (2006.01) |
| *A61B 5/00* | (2006.01) |
| *A61B 5/083* | (2006.01) |
| *G16H 40/67* | (2018.01) |
| *G16H 80/00* | (2018.01) |

(52) U.S. Cl.
CPC .............. *A61B 5/082* (2013.01); *A61B 5/083* (2013.01); *A61B 5/4839* (2013.01); *A61B 5/4842* (2013.01); *A61B 5/4848* (2013.01); *A61B 5/746* (2013.01); *G16H 40/67* (2018.01); *G16H 80/00* (2018.01)

(58) Field of Classification Search
CPC ....... A61B 5/082; A61B 5/083; A61B 5/4839; A61B 5/4842; A61B 5/4848; A61B 5/746; G16H 40/67; G16H 80/00
See application file for complete search history.

(56) References Cited

U.S. PATENT DOCUMENTS

| | | | | |
|---|---|---|---|---|
| 2005/0065446 | A1* | 3/2005 | Talton | G01N 33/497 600/529 |
| 2006/0167722 | A1* | 7/2006 | Mrf Struys | A61B 5/4821 705/3 |
| 2007/0167853 | A1* | 7/2007 | Melker | A61B 5/082 600/532 |
| 2007/0213652 | A1* | 9/2007 | Carter | G16H 40/67 604/20 |

(Continued)

OTHER PUBLICATIONS

International Search Report in International Patent Application No. PCT/US2020/025905 dated Jul. 14, 2020 (7 pp.).

(Continued)

*Primary Examiner* — Patrick Fernandes
(74) *Attorney, Agent, or Firm* — Nixon Peabody LLP

(57) ABSTRACT

The present disclosure is directed to methods and systems that analyze one or more analytes in a fluid, such as breath, emitted from a user. The methods and systems can detect one or more analytes in the breath of a user to provide alerts in response to discrepancies in medications taken by a user, verify one or more medications taken by a user, manage a medication regime of a user, and various other functions disclosed herein.

20 Claims, 10 Drawing Sheets

(56) References Cited

U.S. PATENT DOCUMENTS

| | | | |
|---|---|---|---|
| 2010/0088121 A1* | 4/2010 | Shih | G16H 10/60 |
| | | | 715/780 |
| 2012/0108984 A1* | 5/2012 | Bennett | G16H 50/20 |
| | | | 600/485 |
| 2013/0226079 A1* | 8/2013 | Pesach | G16H 20/10 |
| | | | 604/66 |
| 2014/0100829 A1* | 4/2014 | Mould | G16H 50/50 |
| | | | 703/2 |
| 2014/0278535 A1* | 9/2014 | Romeo | G06Q 10/1095 |
| | | | 705/3 |
| 2014/0322683 A1* | 10/2014 | Baym | G16H 20/13 |
| | | | 340/5.6 |
| 2014/0364758 A1* | 12/2014 | Schindhelm | A61M 16/0666 |
| | | | 600/531 |
| 2017/0074857 A1* | 3/2017 | Dennis | A61B 5/4848 |
| 2017/0332951 A1 | 11/2017 | Ahmad et al. | |
| 2018/0140252 A1 | 5/2018 | Luxon et al. | |

OTHER PUBLICATIONS

Written Opinion in International Patent Application No. PCT/US2020/025905 dated Jul. 14, 2020 (9 pp.).

* cited by examiner

METHODS AND APPARATUSES FOR ANALYZING ONE OR MORE ANALYTES FROM A USER

CROSS-REFERENCE TO RELATED APPLICATIONS

This application is a continuation of International Application No. PCT/US2020/025905, filed on Mar. 31, 2020, which claims priority under 35 § 119 to and the benefit of U.S. Provisional Patent Application Ser. No. 62/902,748, filed on Sep. 19, 2019, U.S. Provisional Patent Application Ser. No. 62/863,095, filed on Jun. 18, 2019, and U.S. Provisional Patent Application Ser. No. 62/827,102, filed on Mar. 31, 2019, each of which is hereby incorporated by reference herein in its entirety.

FIELD OF THE TECHNOLOGY

The present technology relates to the analysis of exhaled breath of a user. The present technology also relates to related systems and their uses, such as a respiratory system capable of analyzing the breath of a user for at least one analyte.

BACKGROUND OF THE TECHNOLOGY

Different forms of respiratory treatment and respiratory treatment apparatuses or systems exist for different respiratory related conditions, such as continuous positive airway pressure (CPAP) apparatuses for users with obstructive sleep apnea (OSA). The positive pressure may be used to prevent collapse of the user's airway during inspiration, thus preventing recurrent apneas or hypopneas and their sequelae. Such a respiratory treatment apparatus can function to generate a supply of breathable gas (usually air, with or without supplemental oxygen) at the therapeutic pressure.

Respiratory treatment apparatuses may typically include a flow generator, an air filter, a mask or cannula, an air delivery conduit connecting the flow generator to the mask, various apparatus sensors and a controller. The flow generator may include a servo-controlled motor and an impeller. The apparatuses' sensors measure conditions of the respiratory treatment apparatuses, including, amongst other things, motor speed, gas volumetric flow rate and outlet pressure, such as with a pressure transducer, flow sensor or the like. The controller may include data storage capacity with or without integrated data retrieval/transfer and display functions.

Users undergoing therapy with respiratory treatment apparatuses often suffer from other physiological conditions or diseases that require monitoring, and in some cases treatment, that are related and/or unrelated to the underlying basis for respiratory treatment.

Sensors, such as biochemical sensors, for detecting various analytes have been developed. Many disease processes create by-products, which may be eliminated from the body through various fluids and through various physiological processes, such as expiration and perspiration. These by-products can be analytes in the form of volatile organic compounds (VOCs) in the breath, or other types of analytes in the breath, saliva, perspiration, and similar bodily fluids. Similarly, substances that users consume are associated with similar analytes in the body. Such substances can include, for example, medications.

As demonstrated by the present technology, there is a need to monitor analytes in the exhaled breath of a user. There may also, or alternatively, be a need for improvement of respiratory treatment apparatuses, and apparatuses and processes in general, for monitoring user conditions, both at a point in time and over longer periods in time. There may also, or alternatively, be a need for improvement of respiratory treatment apparatuses, and apparatuses and processes in general, for monitoring medications that a user consumes, both at a point in time and over longer periods in time.

SUMMARY

Various aspects of the described example embodiments may be combined with aspects of certain other example embodiments to realize yet further embodiments. Other features of the technology will be apparent from consideration of the information contained in the following detailed description, abstract, drawings and claims.

An embodiment of the present technology includes a method for analyzing exhaled breath of a user. The method includes receiving, from at least one sensor positioned in an exhalation path of the user and configured to detect at least one analyte in the exhaled breath of the user, information generated based on the exhaled breath of the user. The method further includes processing the information to determine a presence of the at least one analyte in the exhaled breadth. The method further includes causing a transmission of a message to a remote system based on the determination of the presence of the at least one analyte.

Aspects of the method can include processing the information to determine a concentration of the at least one analyte in the exhaled breadth. Aspects of the method can include the causing of the transmission of the message occurs when the concentration of the at least one analyte satisfies a threshold. Aspects of the method can include the remote system being associated with first responders, and the message indicates at least a potential overdose of the user. Aspects of the method can include the presence of the at least one analyte indicating the user consumed a prohibited substance. Aspects of the method can include the prohibited substance being legally prohibited, medically prohibited, or nutritionally prohibited. Aspects of the method can include the at least one analyte being a metabolite of the prohibited substance. Aspects of the method can include the at least one analyte being peroxynitrite, a volatile organic compound, an isoprostane, or a cytokine. Aspects of the method can include receiving, from the remote system confirmation of receipt of the message. Aspects of the method can include verifying authenticity of the confirmation based, at least in part, on a key transmitted with the confirmation. Aspects of the method can include the at least one sensor being affixed to a frame, and the frame is connected to the user along the exhalation of the path of the user. Aspects of the method can include the frame being a mask of a continuous positive airway pressure device. Aspects of the method can include correlating the determined presence to another metric associated with the user. Aspects of the embodiment can include a system having a control system with one or more processors and a memory having stored thereon machine readable instructions. The control system can be coupled to the memory, and the method and/or any one of the above aspects can be implemented when the machine executable instructions in the memory are executed by at least one of the one or more processors of the control system. Aspects of the embodiment include a system for analyzing exhaled breath of a user. The system includes a control system configured to implement the method and/or any one of the above aspects. Aspects of the embodiment include a computer program product having instructions which, when executed by a computer, cause the computer to carry out the method and/or any one of the above aspects. According to some aspects, the computer program product can be a non-transitory computer readable medium.

Another embodiment of the present technology includes a method for adjusting dosage of an agent. The method includes receiving, from at least one sensor positioned in an exhalation path of a user and configured to detect at least one analyte in exhaled breath of the user, information generated based on the exhaled breath of the user. The method further includes processing the information to determine a presence, a concentration, or a combination thereof of the at least one analyte in the exhaled breadth. The method further includes determining an adjustment to a delivery device configured to deliver the agent to the user based, at least in part, on the presence, the concentration, or a combination thereof of the at least one analyte. The information generated based on the exhaled breath of the user is from multiple discrete measurements during multiple discrete sessions of the at least one sensor detecting the at least one analyte in the exhaled breath of the user.

Aspects of the method can include comparing the information to crowd-sourced information generated based on analysis of exhaled breath of a plurality of additional users being delivered the agent. The determining of the adjustment to the delivery device can be based, at least in part, on the comparison. Aspects of the method can include determining at least one trend in the information across the multiple discrete sessions. The determining of the adjustment to the delivery device can be based, at least in part, on the at least one trend. Aspects of the method can include the adjustment being based on a dosage amount, a dosage frequency, or a combination thereof of the agent. Aspects of the method can include causing a transmission of a message to a remote system requesting the adjustment. Aspects of the method can include the remote system being associated with a healthcare provider associated with the user. Aspects of the method can include the at least one analyte being a metabolite of the agent. Aspects of the method can include the at least one analyte being the agent after being metabolized by the user. Aspects of the method can include the at least one sensor being positioned on a patient interface of a positive airway pressure device, and the at least one analyte being unrelated to respiratory function of the user. Aspects of the method can include instructing the user on how to implement the adjustment to the delivery device via one or more visual instructions presented on a display. Aspects of the embodiment can include a system having a control system with one or more processors and a memory having stored thereon machine readable instructions. The control system can be coupled to the memory, and the method and/or any one of the above aspects can be implemented when the machine executable instructions in the memory are executed by at least one of the one or more processors of the control system. Aspects of the embodiment include a system for analyzing exhaled breath of a user. The system includes a control system configured to implement the method and/or any one of the above aspects. Aspects of the embodiment include a computer program product having instructions which, when executed by a computer, cause the computer to carry out the method and/or any one of the above aspects. According to some aspects, the computer program product can be a non-transitory computer readable medium.

Another embodiment of the present technology includes a method for alerting a user of a potential for a drug interaction. The method includes receiving, from at least one sensor positioned in an exhalation path of the user and configured to detect at least two analytes in exhaled breath of the user, information generated based on the exhaled breath of the user. The method further includes processing the information to determine a presence of a first analyte of the at least two analytes, a presence of the second analyte of the at least two analytes, or a combination thereof in the exhaled breadth. The method further includes generating an alert for the potential of the drug interaction upon determining the presence of the first analyte and the presence of the second analyte in the exhaled breath.

Aspects of the method can include processing the information to determine a concentration of the first analyte of the at least two analytes, a concentration of the second analyte of the at least two analytes, or a combination thereof in the exhaled breadth upon determining the presence of the first analyte and the presence of the second analyte in the exhaled breath. Aspects of the method can include comparing the concentration of the first analyte, the concentration of the second analyte, or a combination thereof to one or more thresholds, and generating the alert for the potential of the drug interaction based on the comparison. Aspects of the method can include generating the alert upon the comparison indicating that the concentration of the first analyte, the concentration of the second analyte, or a combination thereof exceed at least one threshold of the one or more thresholds. Aspects of the method can include generating the alert upon the comparison indicating that the concentration of the first analyte and the concentration of the second analyte exceed at least one threshold of the one or more thresholds. Aspects of the method can include generating the alert upon the comparison indicating that the concentration of the first analyte and the concentration of the second analyte exceed respective thresholds of the one or more thresholds. Aspects of the method can include the at least one sensor being a first sensor and a second sensor, and the first sensor can be configured to detect the first analyte of the at least two analytes and the second sensor can be configured to detect the second analyte of the at least two analytes. Aspects of the embodiment can include a system having a control system with one or more processors and a memory having stored thereon machine readable instructions. The control system can be coupled to the memory, and the method and/or any one of the above aspects can be implemented when the machine executable instructions in the memory are executed by at least one of the one or more processors of the control system. Aspects of the embodiment include a system for analyzing exhaled breath of a user. The system includes a control system configured to implement the method and/or any one of the above aspects. Aspects of the embodiment include a computer program product having instructions which, when executed by a computer, cause the computer to carry out the method and/or any one of the above aspects. According to some aspects, the computer program product can be a non-transitory computer readable medium.

Other embodiments of the present technology include a system and method for analyzing exhaled breath of a user. The system includes at least one sensor positioned in an exhalation path of the user. The at least one sensor configured to detect at least one analyte in the exhaled breath of the user. The system further includes a communication interface, memory, and a control system. The communication interface is configured to communicate with a remote system. The memory contains machine-readable instructions. The control system has one or more processors in communication with the memory. The control system is configured to execute the machine-readable instructions to, and the method includes the steps of, receive, from the at least one sensor, information generated based on the exhaled breath of the user. The control system further is configured to execute the machine-readable instructions to process the information to determine a presence of the at least one analyte in the exhaled breadth. The control system further is configured to execute the machine-readable instructions to cause, via the communication interface, a transmission of a message to the remote system based on the determination of the presence of the at least one analyte.

Other embodiments of the present technology include a system and method for analyzing exhaled breath of a user. The system includes at least one sensor positioned in an exhalation path of the user. The at least one sensor configured to detect at least one analyte in the exhaled breath of the user. The system further includes a communication interface, memory, and a control system. The communication interface is configured to communicate with a remote system. The memory contains machine-readable instructions. The control system has one or more processors in communication with the memory. The control system is configured to execute the machine-readable instructions to, and the method includes the steps of, receive, from the at least one sensor, information generated based on the exhaled breath of the user. The control system further is configured to execute the machine-readable instructions to process the information to determine an absence of the at least one analyte in the exhaled breadth. The control system further is configured to execute the machine-readable instructions to cause, via the communication interface, a transmission of a message to the remote system based on the determination of the absence of the at least one analyte.

Other embodiments of the present technology include a system, apparatus, and/or method for analyzing exhaled breath of a user. The system includes a mask positioned along an exhalation path of the user. The mask is connected to a respiratory device. The system further includes at least one sensor affixed to the mask and positioned in the exhalation path of the user. The at least one sensor is configured to detect at least one analyte in the exhaled breath of the user. The system further includes a communication interface, memory, and a control system. The communication interface is configured to communicate with a remote system, the respiratory device, or a combination thereof. The memory contains machine-readable instructions. The control system has one or more processors in communication with the memory. The control system is configured to execute the machine-readable instructions to, and the method includes the steps of, receive, from the at least one sensor, information generated based on the exhaled breath of the user. The control system further is configured to execute the machine-readable instructions to process the information to determine an absence of a first analyte of the at least one analyte, a presence of a second analyte of the at least one analyte, or a combination thereof in the exhaled breadth of the user. The control system further is configured to execute the machine-readable instructions to cause, via the communication interface, a transmission of a message to the remote system, the respiratory device, or a combination that indicates: (i) the determined absence, (ii) the determined presence, (iii) confirmation of use of the system and lack of the determined absence, the determined presence, or a combination thereof, or (iv) a combination thereof.

Other embodiments of the present technology include a system and method for adjusting a dosage of an agent. The system includes at least one sensor, memory, and a control system. The at least one sensor is positioned in an exhalation path of a user and is configured to detect at least one analyte in exhaled breath of the user. The memory contains machine-readable instructions. The control system has one or more processors in communication with the memory. The control system is configured to execute the machine-readable instructions to, and the method includes the steps of, receive, from the at least one sensor, information generated based on the exhaled breath of the user. The information generated based on the exhaled breath of the user is from multiple discrete measurements during multiple discrete sessions of the at least one sensor detecting the at least one analyte in the exhaled breath of the user. The control system is further configured to process the information to determine a presence, a concentration, or a combination thereof of the at least one analyte in the exhaled breath. The control system is further configured to determine an adjustment to a delivery device configured to deliver the agent to the user based, at least in part, on the presence, the concentration, or a combination thereof of the at least one analyte.

Other embodiments of the present technology include a system, apparatus, and/or method for adjusting dosage of an agent. The system includes at least one sensor, a communication interface, memory, and a control system. The at least one sensor is positioned in an exhalation path of the user and is configured to detect at least one analyte in exhaled breath of the user for a period of time. The communication interface is configured to communicate with a remote system. The memory contains machine-readable instructions. The control system has one or more processors in communication with the memory and is configured to execute the machine-readable instructions to, and the method includes the steps of, receive, from the at least one sensor, information generated based on the exhaled breath of the user. The control system is further configured to process the information to determine a presence, a concentration, or a combination thereof of the at least one analyte in the exhaled breath for the period of time. The control system is further configured to determine one or more trends in the presence, the concentration, or a combination thereof. The control system is further configured to cause, via the communication interface, a transmission of a message to the remote system for notifying a requirement of an adjustment of a dosage of the agent for the user based, at least in part, on the one or more trends.

Other embodiments of the present technology include a system, apparatus, and/or method for acquiring physiological information of a user. The system includes at least one sensor, memory, and a control system. The at least one sensor is positioned in an exhalation path of the user and is configured to detect at least one analyte in the exhaled breath of the user over multiple discrete measurements during multiple discrete sessions. The memory contains machine-readable instructions. The control system has one or more processors in communication with the memory and is configured to execute the machine-readable instructions to, and the method includes the steps of, receive, from the at least one sensor, information generated based on the multiple discrete measurements during the multiple discrete sessions of the at least one sensor detecting the at least one analyte in the exhaled breath of the user. The control system is further configured to process the information to determine a presence, a concentration, or a combination thereof of the at least one analyte in the exhaled breath across the multiple discrete measurements, the multiple discrete sessions, or a combination thereof. The control system is further configured to determine one or more relationships between the presence, the concentration, or a combination thereof of the at least one analyte to one or more physiological parameters, one or more pharmacological parameters, or a combination thereof associated with the user across the multiple discrete measurements, the multiple discrete sessions, or a combination thereof.

Other embodiments of the present technology include a system, apparatus, and/or method for alerting a user of a potential for a drug interaction. The system includes at least one sensor positioned in an exhalation path of the user. The at least one sensor is configured to detect at least two analytes in exhaled breath of the user. The system further includes memory containing machine-readable instructions and a control system. The control system has one or more processors in communication with the memory. The control system is configured to execute the machine-readable instructions to, and the method includes the steps of, receive, from the at least one sensor, information generated based on the exhaled breath of the user. The control system is further configured to execute the machine-readable instructions to process the information to determine a presence of a first analyte of the at least two analytes, a presence of the second analyte of the at least two analytes, or a combination thereof in the exhaled breath. The control system is further configured to execute the machine-readable instructions to generate an alert for the potential of the drug interaction upon determining the presence of the first analyte and the presence of the second analyte in the exhaled breath.

Other embodiments of the present technology include a system, apparatus, and/or method for verifying one or more medications taken by a user. The system includes at least one sensor positioned in an exhalation path of a user. The at least one sensor is configured to detect one or more analytes in exhaled breath of the user. The system includes memory containing machine-readable instructions and a control system. The control system has one or more processors in communication with the memory. The control system is configured to execute the machine-readable instructions to receive, from the at least one sensor, information generated based on the exhaled breath of the user. The control system is further configured to execute the machine-readable instructions to process the information to determine which of the one or more analytes are present in the exhaled breath. The control system is further configured to execute the machine-readable instructions to determine a discrepancy in one or more medications taken by the user based on a discrepancy between the one or more analytes present in the exhaled breath and one or more analytes associated with the one or more medications.

Other embodiments of the present technology include a system, apparatus, and/or method for managing a medication regime of a user. The system includes at least one sensor positioned in an exhalation path of a user. The at least one sensor is configured to detect at least one analyte in exhaled breath of the user. The system further includes memory containing machine-readable instructions and a control system. The control system has one or more processors in communication with the memory. The control system is configured to execute the machine-readable instructions to receive, from the at least one sensor, information generated based on the exhaled breath of the user. The control system is further configured to execute the machine-readable instructions to process the information to determine a presence of an analyte associated with the medication. The control system is further configured to execute the machine-readable instructions to generate an entry regarding the medication within a record associated with the user in response to the presence of the analyte.

DETAILED DESCRIPTION

Figure 1:
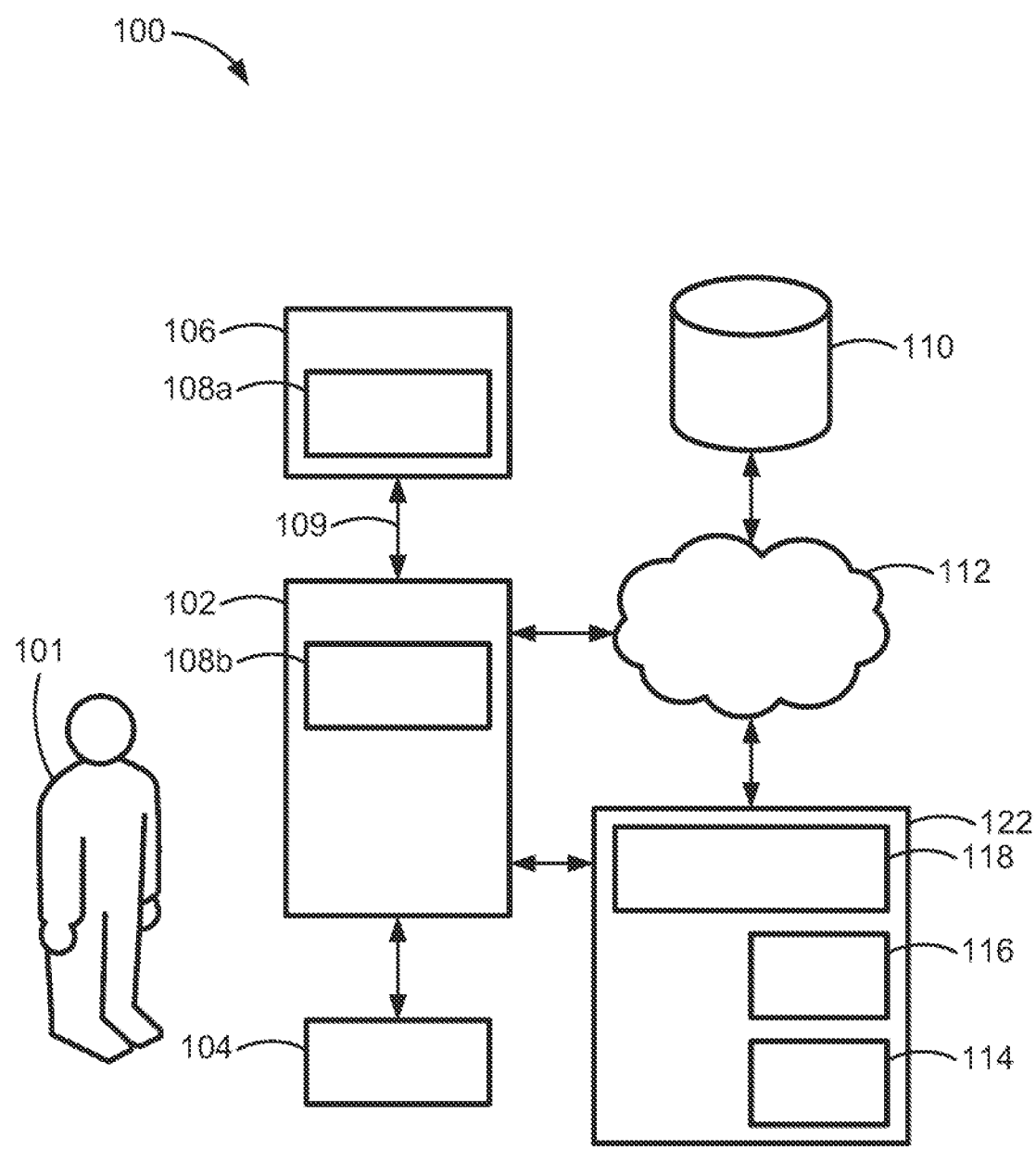
FIG. 1 is a block diagram of an example system for determining information on one or more analytes emitted from a user, according to one embodiment of the present disclosure.

The present technology involves methods and systems for monitoring and detecting various physiological characteristics of a user, and/or treating the user and/or modifying the control of an apparatus, such as a respiratory treatment apparatus, according to those physiological characteristics.

The present technology also involves methods and systems for monitoring and detecting various medications or analytes associated with medications that a user consumes.

The present technology provides methods and systems that capture longitudinal data of breath-based analytes, among other bodily fluids, and derive useful insights from the analytes based, at least in part, on presence and/or concentrations over a period of time. The present technology includes a sensor, a mechanism to capture or direct a user's breath to the sensor, and a mechanism to analyze information generated from the sensor over time, and optionally determine one or more trends over time. From this information, the present technology can determine the useful insights of, for example, the presence of a disease or a drug in the body, the rate the body metabolizes a particular compound of interest, predict potential negative consequences of a particular compound of interest, such as an overdose, and allow for the adjustment of a therapy regime (such as drug dosage or intensity of a medical device mechanism of action). The present technology can also provide for an automatic communication that informs or alerts stakeholders to a user's condition or risk, and a way to aggregate population level data for improved population health management.

With respect to longitudinal data, such data collection provides valuable insights that cannot be gleaned from infrequent spot checks. The placement of the sensor within the present technology provides an unobtrusive way for users to collect valuable biometric data and health information, particularly if the users already use medical devices that reside on the face or in the mouth.

In one or more implementations, the present technology provides for the ability to measure a user's metabolic rate for a given compound, predict a new user's metabolic rate for a given compound based similarities between the user and other users with similar characteristics who have used the system previously, and adjust dosage or delivery rate of a compound, such as a medication, either for therapeutic or recreational use, based on the collected information. The present technology can use one or more algorithms, such as simple regression analysis to complex machine learning, to determine the insights for the individual and/or for whole populations. Indeed, the present technology can use one or more algorithms, such as simple regression analysis to complex machine learning, to perform any of the disclosed methods and processes.

In one or more implementations, the present technology provides for the ability to detect an interaction between two or more medications that a user has taken. The technology can detect two or more analytes in the breath of the user. The analytes indicate the possibility that the user has consumed two more medications that may result in an adverse reaction. The present technology can alert the user of the consumption of such medications so that the user can seek treatment.

In one or more implementations, the present technology provides for the ability to verify medication taken by a user. The present technology provides for analyzing one or more analytes in the breath of the user, either for a single sampling or multiple samplings over time. Based on this analysis, the present technology can verify that the user is or has been taking the medication.

In one or more implementations, the present technology can further provide assistance to the user to aid in the user taking the medication. The assistance can take the form of, for example, one or more reminders to take medication, one or more verifications that the user has taken the medication, information regarding the medication and/or medication dosage, and the like.

In one or more implementations, the present technology uses, at least in part, a respiratory treatment apparatus. Such apparatuses are generally in fluid communication with a user through tubing, and some type of user interface. User interfaces are known to those of ordinary skill in the art and include, but are not limited to, nasal masks, nose and mouth masks, full face masks, nasal pillows and nasal cannulas. In one or more implementations, the user interfaces can include the delivery conduits coupled therewith. The user interfaces can receive airflow from the user's respiratory system via the user's mouth and/or the user's nares. In one or more implementations, the respiratory treatment apparatus can include a vent to provide an intentional leak.

Air is exchanged between a user and a respiratory treatment apparatus via a gas delivery tube or conduit. Generally, the gas delivery tube or conduit attaches to the respiratory treatment apparatus at one end, and the user interface at the other end.

The present technology also employs one or more sensors for the detection of one or more analytes in a fluid from the user, such as breath, saliva, perspiration, and the like. The sensors can be adapted to generate various physiological signals. Such signals can be representative of the analytes in a user that may be attributable to user breath or perspiration. The signals can be processed by one or more processors, such as a processor of the respiratory treatment apparatus, for various analysis of the signals and further processing based on the information contained within the signals.

Different sensors can be employed in different embodiments. For example, detection of increased levels of nitrous oxide in the breath may be indicative of chronic obstructive pulmonary disease (COPD) or asthma. Thus, some embodiments may employ a nitrous oxide sensor. In some embodiments, detection of carbon dioxide ($CO_2$) may be indicative of metabolic or respiratory alkalosis and acidosis. Increased $CO_2$ levels in the breath may also indicate diabetes and renal failure. Thus, some embodiments may employ a $CO_2$ sensor. Low pH may be indicative of many disorders, including asthma and acidosis. Thus, in some embodiments, a pH sensor can be implemented to detect pH levels in the condensate of a user's breath. Similarly, a detection of increased or existing levels of peroxide may be appropriate for users with COPD and asthma to detect inflammation. Thus, in some embodiments, a peroxide sensor can be implemented. For example, an ECoCheck sensor from Carl Reiner GmbH can be implemented. Similarly, a detection of increased or existing levels of lactate may be appropriate for various metabolic conditions. Thus, in some embodiments a lactate sensor may be implemented. In some embodiments, a chemical sensor for detecting ketone bodies may be utilized. In yet another embodiment, at least one of the sensors may be implemented to detect and assess acetone levels in the breath. Acetone levels may be useful in detecting metabolic conditions such as diabetic ketoacidosis.

Exhaled breath condensate in COPD users may be acidified, a condition known as acidopnea. Salivary acids and bases may also be a useful for assessing COPD and other pulmonary inflammatory diseases such as asthma. The presence of acidic volatile substances, such as NH4+ and acetate in saliva, may be indicative of COPD or other inflammatory conditions of the pulmonary system. The presence of nonvolatile cations such as $K^+$ and $Ca_2^+$ may also prove to be useful diagnostic tools. Similarly, the presence of other acids and bases in saliva could be indicative of non-pulmonary related diseases such as GERD. The technology described herein provides devices and sensors for detecting and analyzing various salivary acids and bases, as well as other analytes in saliva.

The one or more analytes can be various analytes associated with various physiological conditions. In accordance with one form of the present technology, the presence of one or more ketones in exhaled breath of a user as the analyte can be used to detect the presence of diabetes and/or metabolic digestion in the user. In accordance with one form of the present technology, the presence of acetone in exhaled breath of a user as the analyte can be used to detect the presence of diabetes and/or metabolic digestion in the user. In accordance with one form of the present technology, the presence of glucose in exhaled breath of a user as the analyte can be used to detect the presence of diabetes in the user. In accordance with one form of the present technology, the presence of insulin in exhaled breath of a user as the analyte can be used to detect the presence of diabetes in the user. In accordance with one form of the present technology, the presence of one or more of Leukotriene B4, Interleukin 6 and $H_2O_2$ in exhaled breath of a user as the analyte can be used to detect the presence of one or more of oxidative stress, asthma, diabetes and COPD in the user. In accordance with one form of the present technology, the presence of high-sensitivity C-reactive protein (hs-CRP) in exhaled breath of a user as the analyte can be used to detect the presence of cardiac autonomic control in the user. In accordance with one form of the present technology, the pH of exhaled breath of a user can be used to detect the presence of asthma or bronchitis in the user. In accordance with one form of the present technology, the conductivity of exhaled breath of a user can be used to detect the presence of asthma or bronchitis in the user.

In one or more implementations, the analyte can be a substance that the user consumed, such as a medication, or a metabolite of a substance that the user consumed. For example, the analyte can be ethanol in response to the user drinking an alcoholic beverage. The analyte can alternatively be a compound or element present in breath that indicates a disease or other medical condition, or the potential onset of a disease or medical condition. For example, the analyte can be nitric oxide (NO) that can indicate asthma. As discussed above, exemplary analytes can include organic and inorganic gases, such as the NO, carbon dioxide ($CO_2$), carbon monoxide (CO); and/or volatile organic compounds (VOCs), such as acetone, formaldehyde, and ketones; and/or other non-volatile compounds, such as cytokines, isoprostanes, and peroxynitrite.

Certain analytes may be in significant enough quantities to be detected in real time and processed by the system. In contrast, some analytes (e.g., immunological markers and pH) may only appear in trace amounts. For example, analytes detectable in trace amounts may be collected over a period of time. Once the collection period is complete, the analysis may be conducted with a sensor controlled by the respiratory treatment apparatus as described herein. Optionally, the timed collection period may be associated with the amount of use of the treatment apparatus (e.g., a time of operation of the treatment apparatus). Optionally, the timed collection period may correspond to a number of breaths made by a user into a collector. In some cases, the activation of the sensor may be coordinated with user respiration. For example, the sensor may be triggered for sensing only during user expiration.

The sensors of the present technology can be various types of nanodetectors, such as those developed by Applied Nanodetectors, and in particular infrared spectroscopic detection. In some cases, such sensors may optionally employ metal oxide or "MOx" receptors. Other types of sensors may include those employing the use of spectroscopic or light analysis, which can be useful to sense analytes such as acetone. In embodiments of the present technology, spectroscopic detection may be used in conjunction with an external, light emitting source.

In one or more embodiments, the present technology can be implemented to detect an analyte for a single measurement. Alternatively, or in addition, the present technology can be implemented to detect an analyte for a plurality of measurements over an extended period of time. For example, in one or more implementations, a sensor can generate information based on the exhaled breath of the user for multiple discrete measurements during multiple discrete sessions of the sensor detecting the at least one analyte in the exhaled breath of the user.

In the present technology, sensing may be conducted and analyzed by one or more processors, such as the controller of a respiratory treatment apparatus, one or more processors in a computer device, and/or or one or more processors in a back-end server or of a cloud computing architecture. The processors disclosed herein can compare information derived from the signal(s) of the one or more sensors to one or more thresholds. Suitable thresholds for detection may be determined empirically such that the comparison may be indicative of different disease conditions or changes in disease conditions that relate to the detection capabilities of the sensors.

Based on the detection of the presence and/or concentration of an analyte, or a trend of the same, satisfying one or more thresholds, one or more actions can occur, as provided in the following description. In one or more implementations, a message can be generated on a display, a reminder can be added to a calendar, audio or visual information can be presented to the user, or an audio alarm can trigger a recommendation to seek medical help, such as in response to a detected drug interaction or overdose. In some implementations, the information may be transmitted by wired or wireless communication to the user's healthcare provider. In some implementations, and depending on the nature of the detected condition or event, the respiratory treatment apparatus may generate or trigger an automatic emergency telephone call (e.g., a 911 call) and play an automated voice message such as with a name, an address, and a detected condition or information, such as a detected potential interaction or overdose, to request more immediate help by phone.

FIG. 1 is a block diagram of an example system 100 for analyzing one or more analytes from a user 101 and performing an action in response thereto, representing one embodiment of the present technology. The action that is performed in response thereto can vary. In one or more embodiments, the action can include, for example, adjusting the dosage of an agent administered to the user 101, alerting the user 101 of a potential for a drug interaction, verifying one or more medications taken by the user 101, managing a medication regime of the user 101, or any other method or response described in the present disclosure.

The system 100 of FIG. 1 includes the user 101 connected to a respiratory treatment apparatus 102 via a user interface 106. The user interface 106 can include a sensor 108a as described above that can generate information based on detecting one or more analytes emitted from the user 101, such as from the user's breath. Thus, in one or more implementations, the sensor 108a and the user interface 106 are configured to be positioned in an exhalation path of the user 101. Alternatively, a sensor 108b, such as any sensor discussed above that is configured to detect an analyte within the breath of the user 101, can be attached to and/or integrated within the respiratory treatment apparatus 102. As shown, the sensor 108 (which for convenience refers to one or both of the sensors 108a and 108b) can be in electronic communication with the respiratory treatment apparatus 102.

Although only two sensors 108a and 108b are illustrated in FIG. 1, one or more implementations of the system 100 can include more than the two sensors 108a and 108b. In such embodiments, or in the case illustrated in FIG. 1, each sensor 108 can be configured for a different, specific analyte, or each sensor 108 can be configured for one or more of the same analytes. In one or more implementations, having multiple sensors 108 for the same analyte provides redundancy, which can improve the accuracy of the system 100.

In one or more implementations, the analyte can be a direct indicator of a consumed substance or a physiological condition. Alternatively, or additionally, the analyte can be an indirect indicator of a consumed substance or a physiological condition. For example, as discussed above, the analyte can be a metabolite of a consumed substance, such as a metabolite of a medication taken by the user. In one or more implementations, the analyte can be correlated to a substance of interest, but not necessarily a metabolite of the consumed substance. For example, a consumed substance may cause a chain reaction and the analyte may be one result along the chain reaction, although not per se a direct metabolite. One example of this is using hydrogen gas as the analyte for measuring the amount of carbon dioxide present in exhaled breath because there is a correlation between the two gases—although hydrogen gas is not a metabolite of carbon dioxide. More specifically, a carbon dioxide sensor can be rather expensive. For applications that do not require high accuracy, it is possible to measure hydrogen instead because there is a correlation between the two gasses in human breath.

Collecting a reproducible, non-contaminated sample of exhaled breath is non-trivial and can be influenced by ambient air conditions, user behavior and breathing patterns, and interactions with sampling system materials. In one or more implementations, the system 100 can include an environmental sensor 104. The environmental sensor 104 can be identical to the sensor 108. However, the environmental sensor 104 is not positioned in the exhalation path of the user 101 and, therefore, does not generate information based on the exhaled breath of the user 101. Instead, the environmental sensor 104 is configured to measure the ambient air composition and generate ambient information. The respiratory treatment apparatus 102 can then process the ambient information to ensure that the measurement of exhaled breath reflects only the effects of the user 101 rather than any contamination from the ambient air.

Although the user interface 106 is described throughout as being, for example, nasal pillows, a nasal mask, a full-face mask, and the like, in one or more embodiments, the user interface 106 can be any other structure that positions the sensor 108 within the exhalation path, such as a frame of the user interface 106 or of another device positioned near the exhalation path of the user 101.

In one or more implementations, the sensor 108 can be positioned in the user 101's exhalation path directly, such as by positioning the sensor 108 near or in the nose and/or mouth of the user 101. For example, the sensor 108 can be affixed to a face-mounted frame user interface 106, such as a nasal mask or a full-face mask. Alternatively, the user interface 106 may be a mouth-mounted device, such as a mouth guard, with the sensor 108 placed within the mouth. Alternatively, the sensor 108 may be placed within an exhalation path created by the mouth guard, such as a small hole or tube exiting the mouth. In one or more embodiments, the sensor 108 can be positioned on a limb that extends from the mouth guard such that the sensor 108 is positioned in the exhalation path of, for example, a user's nose.

Alternatively, in one or more implementations, the sensor 108 can be positioned in the user's exhalation path indirectly, such as by positioning the sensor 108 away from the user's nose and mouth but directing the user's exhaled breath towards the sensor 108. In such implementations, the user interface 106 can have one or more features that direct the user's breath to the sensor 108. For example, the user interface 106 can be a breath capture device, such as a mask or nasal pillows, with a preferred exhalation path, such as a one-way valve to create an exhaust port, with tubing connected to the exhaust port leading to the sensor 108.

Although the respiratory treatment apparatus 102 is described throughout as performing the processing of the information generated by the sensor 108, in one or more embodiments, the processing of the information generated by the sensor 108 can instead be performed by a user computing device 122 associated with the user 101 and separate from the respiratory treatment apparatus 102. The user computing device 122 is configured to process information from the sensor 108 and communicate with a remote system 110 over the network 112, discussed below. The user computing device 122 may be a personal computer, a mobile phone, a tablet computer, or various other smart computing devices, such as devices with one or more processors that can execute machine-readable instructions stored in local or remote memory.

The user computing device 122 includes at least memory 114, one or more processors 116, and a communication interface 118. The memory 114 stores machine-readable instructions for causing one or more of the operations disclosed herein. The memory 114 can be, for example, dynamic memory (e.g., RAM, magnetic disk, etc.) and/or static memory (e.g., ROM, CD-ROM, etc.).

The one or more processors 116 can be implemented via software, hardware, firmware or a combination of software and/or firmware and/or hardware. For example, the processes described herein may be advantageously implemented via processor(s), Digital Signal Processing (DSP) chip, an Application Specific Integrated Circuit (ASIC), Field Programmable Gate Arrays (FPGAs), etc. Such exemplary hardware for performing the described functions is detailed below. The one or more processors 116 perform a set of operations on information as specified by the machine-readable instructions related to analyzing information from the sensor 108 and performing one or more actions in response to the analysis, such as generating a message that is transmitted to a remote system (e.g., remote system 110). The machine-readable instructions are a set of instructions or statements providing instructions for the operation of the one or more processors 116 and/or the user computing device 122 to perform specified functions. The instructions, for example, may be written in a computer programming language that is compiled into a native instruction set of the one or more processors 116. The code may also be written directly using the native instruction set (e.g., machine language). The set of operations typically include comparing two or more units of information, shifting positions of units of information, and combining two or more units of information, such as by addition or multiplication or logical operations like OR, exclusive OR (XOR), and AND.

Although described as being part of the user computing device 122, in one or more implementations, the one or more processors 116 can be located remote from the sensor 108 and the user 101, such as for a cloud-based computing arrangement. In which case, the sensor 108 can be located with the user 101 for generating the information based on the exhaled breath.

The user computing device 122 communicates with a remote system 110 via a network 112 through the communication interface 118. The communication interface 118 provides a two-way data communication coupling for the user computing device 122. For example, the communication interface 118 may be configured for wired or wireless communications with the network 112. The network 112 could be any standard network, such as cellular network, a WiFi network, a Bluetooth network, a wide area network (WAN), the Internet, or any other communications network. Although a single communication interface 118 is depicted in FIG. 1, multiple communication interfaces can also be employed. The user computing device 122 can send information to and from the network 112 through the communication interface 118. In the example of the Internet, a server (not shown for illustrative convenience) might transmit requested code belonging to an application program for implementing an embodiment of the invention through the communication interface 118.

As discussed above, in one or more implementations, the sensor 108 communicates with the user computing device 122 via the communication interface 118, such as in the form of a local (wired or wireless) communications protocol, such as a local network protocol (e.g., Bluetooth). In one or more alternative embodiments, the sensor 108 can communicate with the user computing device 122 via the network 112, depending on the sophistication of the sensor 108. For example, the sensor 108 can be WiFi-enabled so as to be able to connect to the network 112 for communicating with the user computing device 122.

The remote system 110 can be a remote computing system operated by one or more third parties. In one or more implementations, the third parties can be first responders, healthcare providers associated with the user 101, nutritionists associated with the user 101, any guardian, custodian, or authoritative figure associated with the user 101 (e.g., parent, adult child, probation officer, police, etc.), pharmacists associated with the user 101, and the like. The remote system 110 is configured to receive messages from the user computing device 122 and is configured to store the messages and/or transmit messages back to the user computing device 122, as further described below. In one or more implementations, the remote system 110 can have one or more processors, memory, and a communication interface similar to the user computing device 122 for performing the below operations.

Although only one remote system 110 is shown in FIG. 1, the system 100 may have more than one remote system 110. For example, there may be a remote system 110 associated with each one of the different types of third parties associated with the user 101.

In some implementations, the remote system 110 may carry out some post-processing of the information contained within the messages, such as with one or more processors in communication with or included in the remote system 110. One example of such post-processing is to transmit a confirmation of receipt of the message. The post-processing can further include various operations for authenticating communication with the user computer device 112.

The system 100 may contain other devices (not shown) associated with other respective users (not shown) who also have respective associated user computing devices (not shown).

Figure 2:
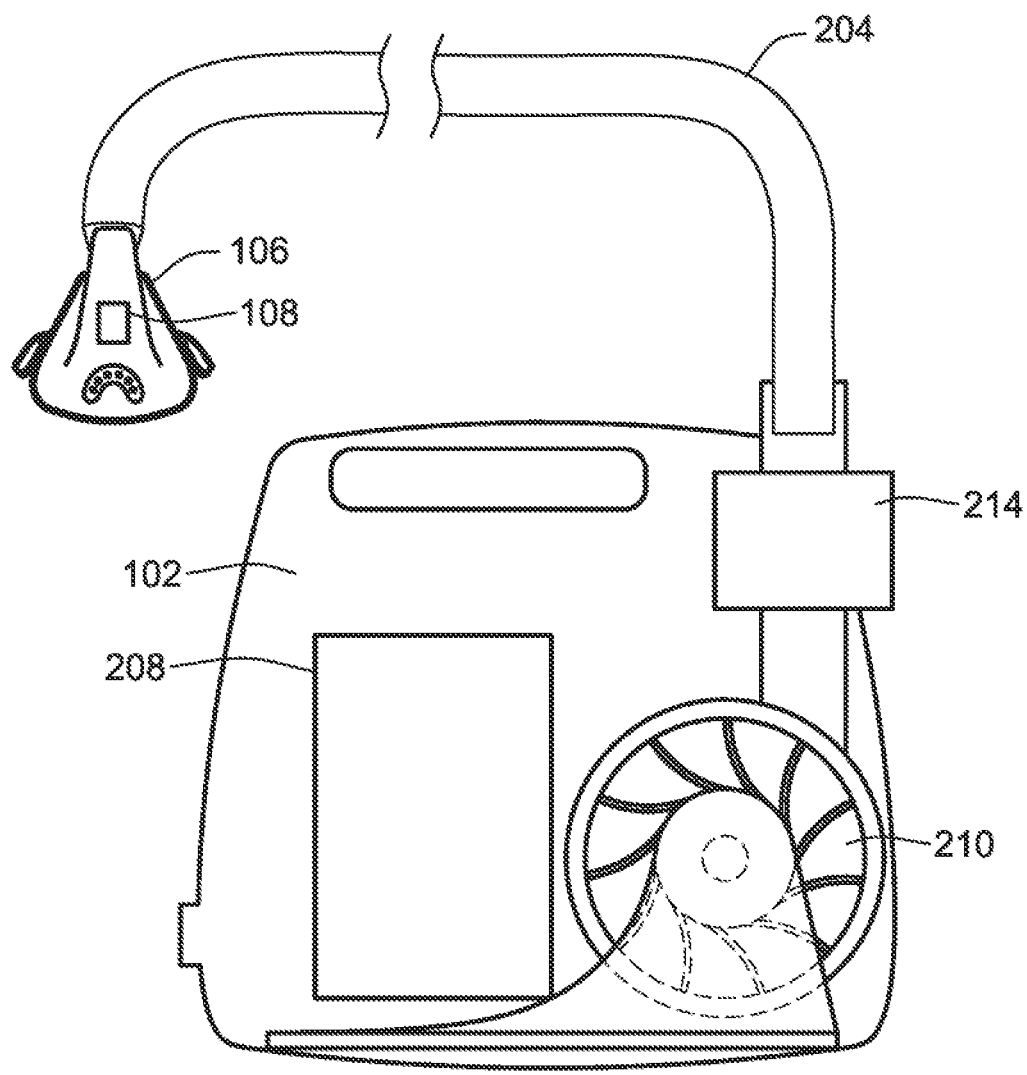
FIG. 2 is an example respiratory treatment apparatus having a sensor and a controller, according to one embodiment of the present disclosure.

FIG. 2 depicts an example of a respiratory treatment apparatus 102. The respiratory treatment apparatus 102 contains a controller 208 and a flow generator 210. The respiratory treatment apparatus 102 is connected to a tube 204 that is in fluid communication with the user interface 106. The user interface 106 contains the sensor 108 that is in electronic communication with the respiratory treatment apparatus 102.

In one or more implementations, the respiratory treatment apparatus 102 or the user interface 106 may also include a drug delivery device 214 for delivering an agent to a user. For example, the drug delivery device 214 can be an aerosolized delivery system. The drug delivery device 214 may be prefilled with an agent specific for the user, such as a specific medication. The respiratory treatment apparatus 102 may control the delivery of the agent based on one or more specific signals. For example, upon receiving a signal from the controller 208, the agent may be released by the drug delivery device 214 into the tube 204, which then travels to the user 101 (FIG. 1) within the user interface 106. Thus, the agent can be released into the stream of air administered to the user 101 during the inspiratory phase of respiration.

Figure 3:
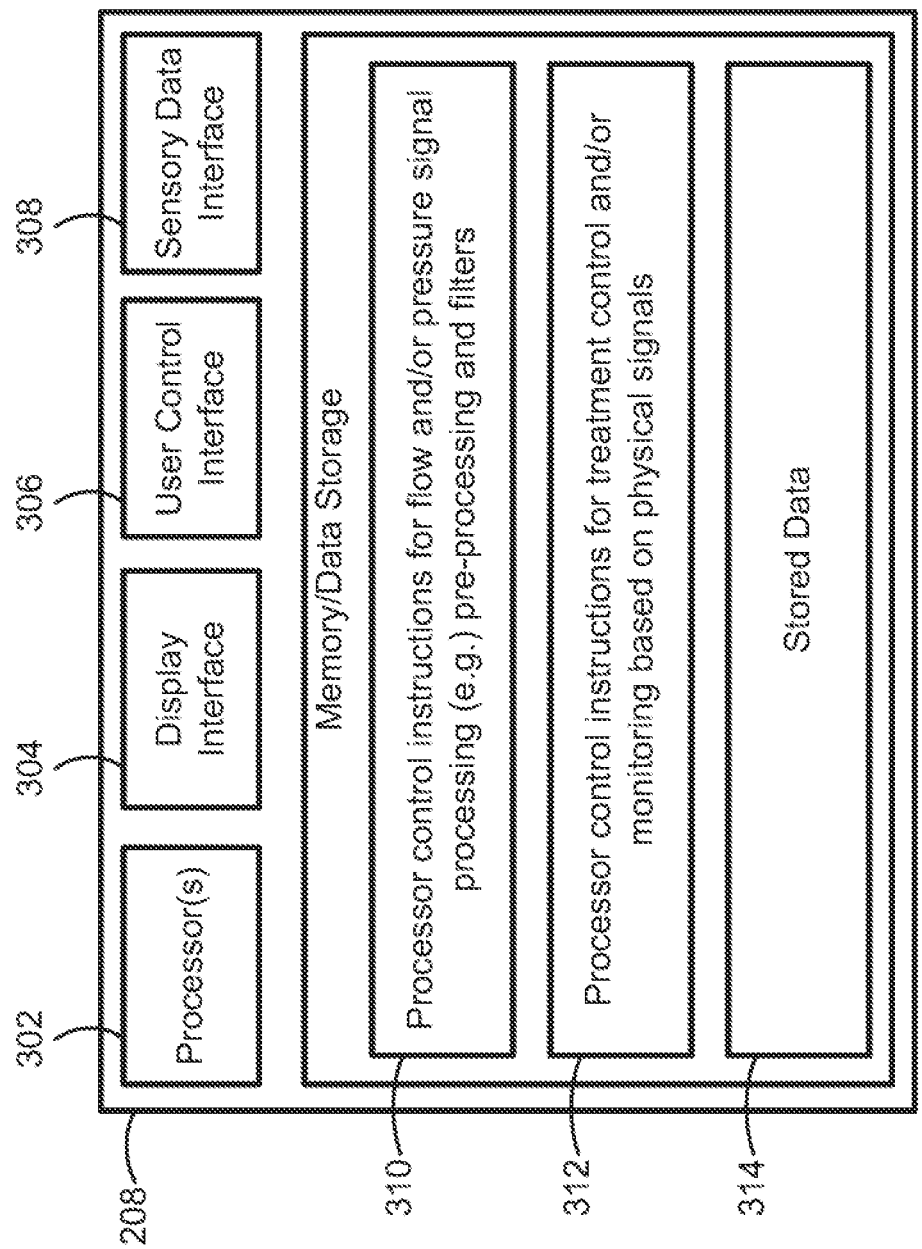
FIG. 3 is a block diagram depicting various components of a controller of the present technology, according to one embodiment of the present disclosure.

FIG. 3 illustrates an example system architecture of the controller 208 suitable for the present technology in block diagram form. In the illustration, the controller 208 may include one or more processors 302 for physiological signals, as well as the respiratory treatment apparatus 102. Alternatively, the controller 208 may include more than one processor 302, with each processor 302 to be used for processing different types of data, or to increase the computing power of the overall controller 208. The controller 208 may also include a display 304 to output event detection reports (e.g., respiratory rate, heart rate variability, analyte profiles, etc.), results or graphs such as on a monitor or LCD panel, or other information, such as medication information or dosage instructions. In one or more implementations, the display 304 can include one or more warning lights (e.g., one or more light emitting diodes) or a display screen, such as a liquid crystal display (LCD). In one or more implementations, the display 304 can be controlled to show information derived from the physiological signals.

A user control/input interface 306, such as a keyboard, touch panel, control buttons, mouse, etc., may also be provided to activate or modify the control methodologies described herein. The controller 208 may also include a sensor or data interface 308, such as a bus, for receiving/transmitting data such as programming instructions, pressure and flow signals, facial physiological signals, breath collection related signals, breath chemical signals, cardiac signals, etc. The controller 208 may also typically include memory/data storage components containing control instructions of the methodologies discussed herein. These may include processor control instructions 310 for flow and/or pressure signal processing (e.g., pre-processing methods, filters, etc.). These may also include processor control instructions 312 for treatment control and/or monitoring based on signal detection (e.g., nitrous oxide, $CO_2$, acetone, pH, pathogens, etc.). Finally, the controller 208 can also include stored data 314 for these methodologies such as physiological signals, historic lookup data, critical thresholds, zone maps to determine "danger zones," etc.

In some embodiments, these processor control instructions and data for controlling the above described methodologies may be contained in a computer-readable storage medium as software for use by a general-purpose computer so that the general purpose computer may serve as a specific-purpose computer, according to any of the methodologies discussed herein, upon loading and executing the software in the general-purpose computer.

While the physiological signal detection technology has been described in several embodiments, it is to be understood that these embodiments are merely illustrative of the technology. Further modifications may be devised within the spirit and scope of this description. For example, while an integrated apparatus is contemplated by the present technology, the methodology of the components of the apparatuses described herein may be shared across multiple components of a system. For example, a controller may simply measure the signals of the user and transfer the data representing those signals to another processing system. The second processing system, such as a remote system 110, may in turn analyze the data to determine the signal or related data and metrics therefrom. The second processing system may then evaluate the data and generate warning messages as described herein, such as by sending one or more of the messages described herein, in electronic form for example, back to the user monitoring device for presentation on the display 304 to warn the user, or perform any other functionality discussed herein. Other variations can be made without departing with the spirit and scope of the technology.

Figure 4:
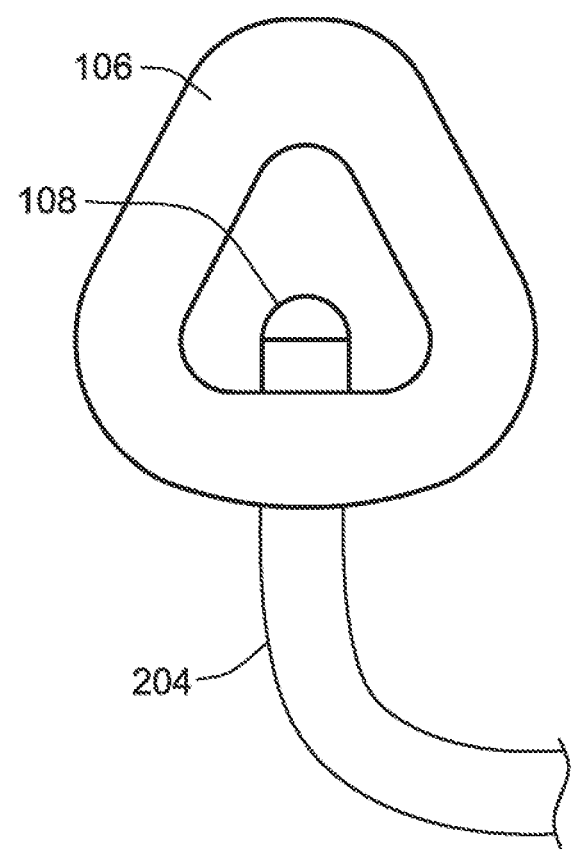
FIG. 4 is a front view of a respiratory treatment mask containing a physiological sensor attached to the end of a gas delivery tube, according to one embodiment of the present disclosure.
Figure 5:
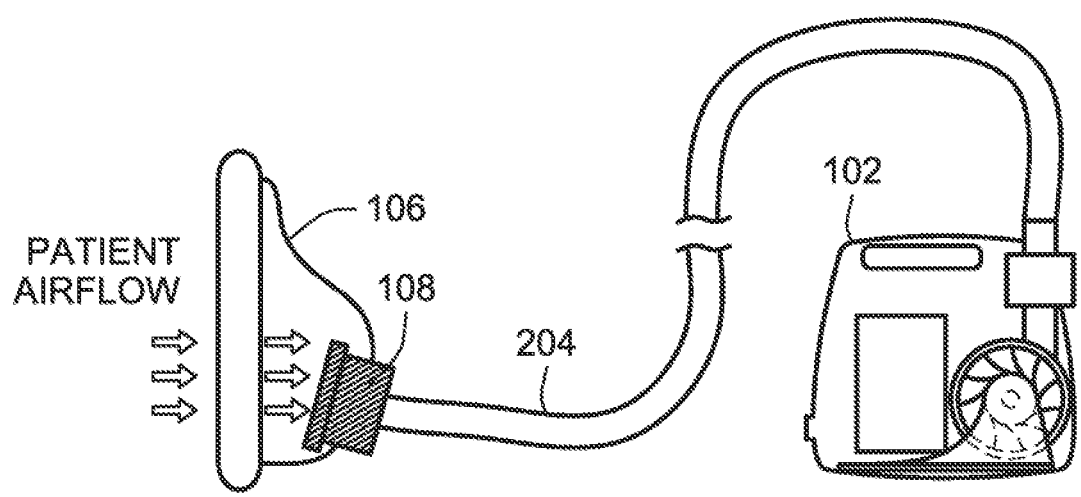
FIG. 5 is a left side view of the respiratory treatment mask of FIG. 4, according to one embodiment of the present disclosure.

FIGS. 4 and 5 depict an example of the sensor 108 mounted within the user interface 106. The sensor 108 may be positioned proximate to the user's mouth to directly receive the user's exhaled breath from within the user interface 106. In this embodiment, the sensor 108 is mounted on one side of the gas delivery tube or conduit 204, which attaches to respiratory treatment apparatus 102.

In one or more embodiments, the sensor 108 may also be configured to assess samples of saliva from the user interface 106. These saliva samples may be analyzed for the presence or absence of volatile and nonvolatile analytes, which may include but are not limited to $NH_4^+$, acetate, $K^+$ and $Ca_2^+$, or any other disclosed agent.

Figure 6:
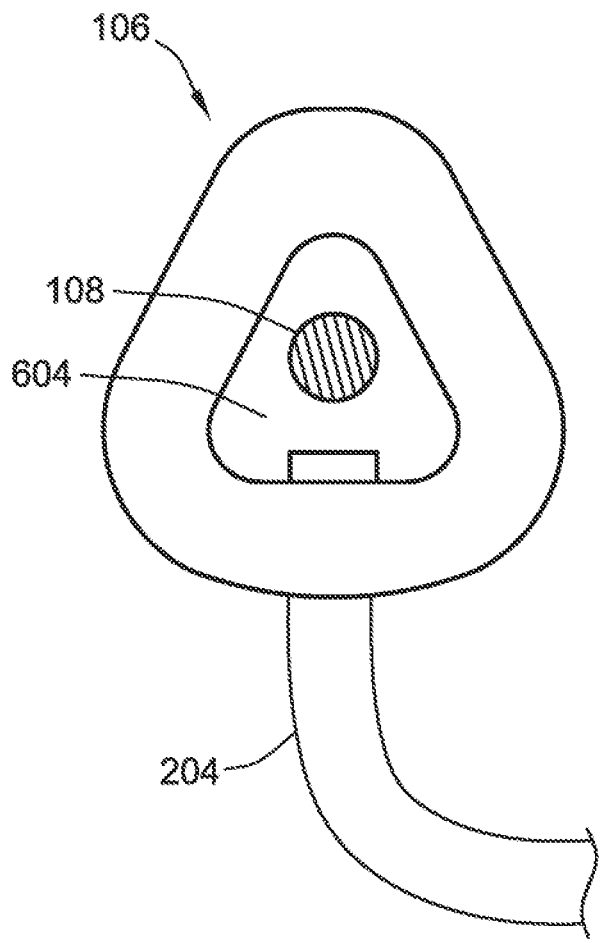
FIG. 6 is a front view of a respiratory treatment mask containing a physiological sensor attached to the frame of the mask, according to one embodiment of the present disclosure.
Figure 7:
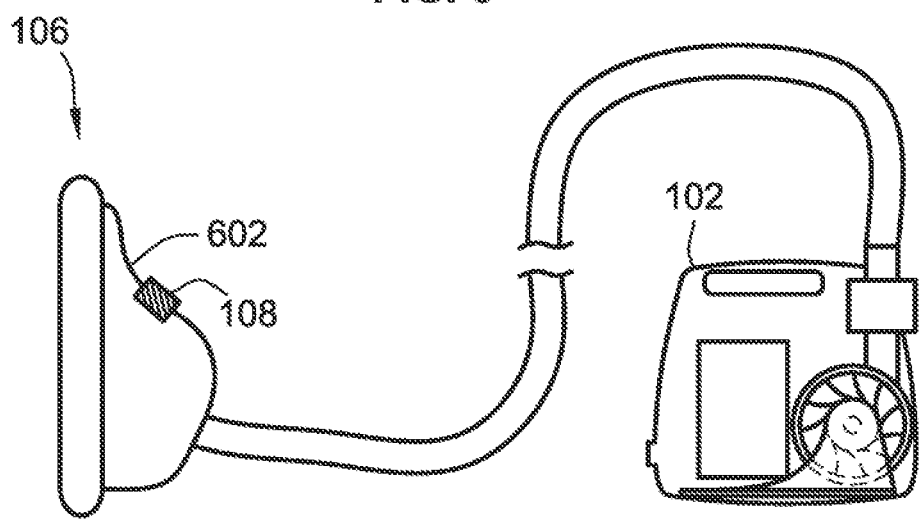
FIG. 7 is a left side view of the respiratory treatment mask of FIG. 6, according to one embodiment of the present disclosure.

FIGS. 6 and 7 depict further examples of the present technology where the sensor 108 is contained in the frame 602 of a user interface 106. Unlike the device depicted in FIGS. 4 and 5, the sensor 108 in this example is contained within the frame 602 of a user interface 106, without being connected to the gas delivery tube or conduit 204.

The present technology may be configured in various ways to transmit the electronic signal from the physiological sensor(s), to the respiratory treatment apparatus. The sensors utilized in the present technology may have outgoing electronic circuitry (e.g., circuitry in FIG. 1) to transmit signals or data regarding information collection. The outgoing circuitry may be configured with the tube 204. A configuration of outgoing electronic circuitry that relies on wires for data transmission is referred to herein as a "wired solution."

However, in some embodiments, the sensors themselves may be implemented with components for transmitting the signals to the controller or signal detection processor by wireless communication. For example, the signals interface of the controller 208 (FIG. 2) may include a receiver or transceiver to communicate wirelessly with one or more transmitters or transceivers integrated with the sensors 108. In such a case, data representing the signals can be transmitted digitally, for example, by any suitable wireless protocol, such as Bluetooth. Optionally, a set or array of sensors may share a common transmitter or transceiver for transmission of the data of several sensors to the controller. This approach to data transmission in the present technology is referred to herein as a "wireless solution."

Figure 8:
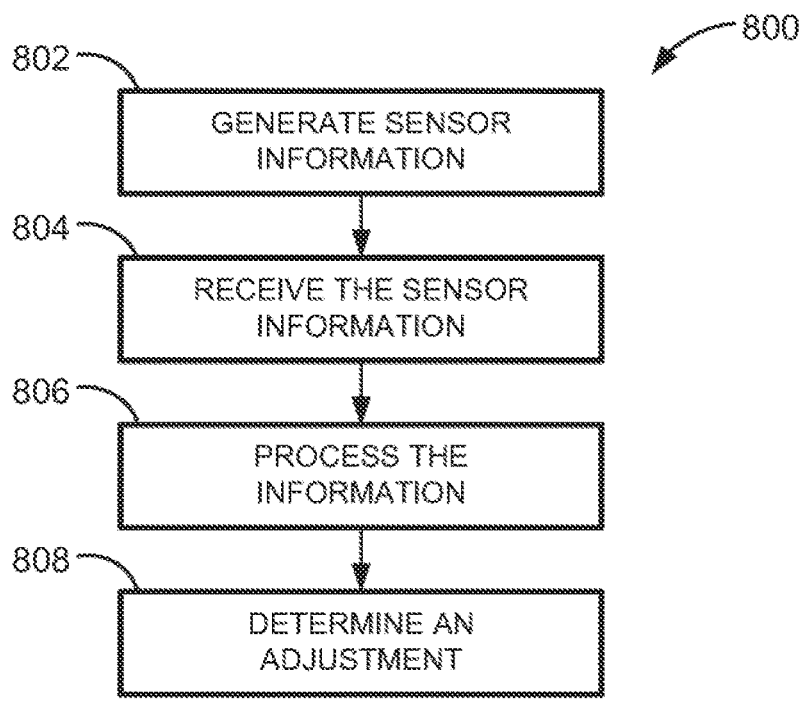
FIG. 8 is a flow diagram of a process for analyzing exhaled breath of a user and determining an adjustment to a delivery device, according to one embodiment of the present disclosure.

FIG. 8 illustrates an example of a process 800 for analyzing exhaled breath of a user 101 and determining an adjustment to a delivery device 214. The process 800 can be performed by implementing one or more of the elements of the system 100 in FIG. 1.

First (802), the sensor 108 (or at least one sensor) that is positioned in an exhalation path of the user 101 and configured to detect at least one analyte in the exhaled breath of the user 101 generates information on the exhaled breath. The information can indicate the presence or absence of the analyte in the breath, the concentration of the analyte, or a combination thereof. The sensor 108 can generate the information continuously, periodically, or on demand. For example, the sensor 108 can generate the information multiple times during each breath of multiple continuous breaths, or once for each breath of the multiple continuous breaths. Alternatively, the sensor 108 can generate the information periodically, such as once every minute, once every hour, once a night, etc. Alternatively, the sensor can generate the information upon receiving a request (e.g., from the user or from the remote system, etc.). The request can indicate the number and time for generating the information based on the exhaled breath, such as for each exhaled breath, once a specified number of breaths, etc.

The sensor generates longitudinal data by generating the information based on the exhaled breath of the user for multiple discrete measurements during multiple discrete sessions of the at least one sensor detecting the at least one analyte in the exhaled breath of the user. Thus, the information is generated from the sensor over a period of time, rather than just for one discrete measurement. The longitudinal data allows the system 100 to perform various actions that rely on more than just one sampling point, such as determining an adjustment to a delivery device 214 as further described below.

As discussed above, the sensor 108 can be affixed to a frame, and the frame can be connected to the user 101 so as to position the sensor 108 along the exhalation of the path of the user 101. Although the sensor 108 can be affixed to a user interface 106 of a respiratory treatment apparatus 102, in one or more implementations, the at least one analyte can be unrelated to respiratory function of the user. Instead, the at least one analyte can be related to any of the physiological functions and/or disorders discussed herein.

As discussed above, the delivery device 214 can administer an agent to the user 101. In one or more implementations, the at least one analyte can be a metabolite of the agent. Alternatively, in one or more implementations, the at least one analyte can be the agent itself. Accordingly, the information generated from the sensor 108 can provide information on how the user is responding to the agent.

Next (804), a controller (e.g., the one or more processors 116 of FIG. 1, or the controller 208 of FIG. 2) receives information generated by the sensor 108 based on the exhaled breath of the user. Similar to the generation of the information, transmission of the information by the sensor to the controller can be continuous, periodic, or on demand. In one or more implementations, the information can include data only related to the presence of the analyte. Alternatively, in one or more implementations, the information can include other information, such as demographic data, profile data, sensor type, and other types of data.

Next (806), the controller (e.g., the one or more processors 116 of FIG. 1, or the controller 208 of FIG. 2) processes the information to determine the presence, the concentration, or a combination thereof of the at least one analyte in the exhaled breath. With respect to determining the presence, the processing may include simply determining the value of a bit within the information that provides a binary indication of the presence of the analyte. For example, the bit being 1 can indicate that the analyte was present in the exhaled breath, and the bit being 0 can indicate that the analyte was not present in the exhaled breath. The information may contain multiple different bits providing binary indications for multiple different analytes depending on the functionality of the sensor 108.

In one or more implementations, the information may be more granular, such as degrees of presence. For instance, the information can indicate whether the analyte is (i) not detected, (ii) detected in a quantity typical for error or noise, (iii) detected in a quantity that indicates the presence of the analyte, or (iv) detected in such a large quantity that may indicate an error in the system 100, such as an error in the sensor 108. Examples of large quantities may include quantities that are not physically possible, such as ethanol levels that are beyond the ability for human consumption of alcohol. The granularity may be even more specific such that the information includes both the presence of the analyte and the concentration of the analyte.

However, in one or more embodiments, the information may include only the concentration. The information may include the concentration directly, such that the processing entails retrieving the concentration from the information. Alternatively, the information may include the quantity of the analyte, such as the number of moles, microns, parts per million (ppm) of the analyte found in the exhaled breath, in addition to the volume of exhaled breath that was sampled to obtain the information. In one or more implementations, the information generated from the sensor 108 may include only the quantity, and the volume of exhaled breath may be acquired from another sensor, or from another device. For example, the volume of sampled air may be obtained from the respiratory treatment apparatus 102. Thus, the processing of the information can include information from both the sensor 108 and the user computing respiratory treatment apparatus 102.

In one or more implementations, the processing can include comparing the concentration to one or more metrics associated with the user. The metrics can be physiological metrics that, when combined with the concentration of the analyte, provide greater insight into appropriate actions to be taken. For example, comparing the concentration to the metrics allows for the tailoring of the specific responses to the presence determination. Such metrics can include binary metrics, such as whether the user is a diabetic. Such metrics can be more granular, such as physiological parameters including the weight, height, body mass index, and/or age of the user.

In one or more implementations, the processing can include comparing the information from the sensor 108 to ambient information from the environmental sensor 104. This comparison allows for accounting for the ambient air surrounding the user 101.

In response to the concentration of the analyte, the processing may include comparing the concentration to one or more thresholds. The thresholds correlate the concentration to predetermined actions to be taken, such as in the event of a presumption of a medical emergency based on the concentration of the analyte.

Because the information represents longitudinal data from the user 101 over a period of time, the processing described above for each one or both of the presence and the concentration can occur for each specific presence and concentration data point. As a result, trends can appear in the data with respect to the presence and/or concentration. The system 100 can then perform additional functionality based on the trends that are not possible otherwise with only a single data point of presence and/or concentration.

Next (808), the controller (e.g., the one or more processors 116 of FIG. 1, or the controller 208 of FIG. 2) determines an adjustment to an agent delivery device 214 configured to deliver an agent to the user based, at least in part, on the presence, the concentration, or a combination thereof of the at least one analyte. The adjustment can be based on a dosage amount, a dosage frequency, or a combination thereof of the agent. The adjustment to the delivery device 214 is based on the presence, the concentration, or both over the period of time associated with the longitudinal data. Accordingly, the adjustment can take into account the trends within the longitudinal data, that may account for or represent the efficacy of treatment of the agent, such as requiring less or more agent based on the lack of effect or too much effect. Moreover, the adjustment is based on more than just a single measurement of presence and/or concentration such that the adjustment can take into account potential variations that are unrelated to the efficacy of the agent.

In one or more implementations, the one or more processors 116 can compare the information to crowd-sourced information generated based on analysis of exhaled breath of a plurality of additional users being delivered the agent. In which case, the adjustment to the delivery device can be based, at least in part, on the comparison. Such a comparison can relate how the plurality of additional users responded to the adjustment. The plurality of additional users can be users that have similarities to the user. Such similarities can be one or more similar physiological parameters, such as age, gender, weight, height, ethnicity, medical conditions, social behaviors, etc.

In one or more implementations, the comparison can be based the plurality of users having received similar adjustments to the same agent such that the system 100 can estimate or predict the response the user will have to the adjustment based on the responses the plurality of users had.

In one or more implementations, the controller (e.g., the one or more processors 116 of FIG. 1, or the controller 208 of FIG. 2) can have a communication interface 118 (FIG. 1) configured to communicate with a remote system 110 (FIG. 1). The remote system 110 can be associated with, for example, a healthcare provider associated with the user 101. The controller can be configured cause a transmission of a message to the remote system requesting the adjustment. For example, any adjustment to the delivery device may require approval from the healthcare provider. Thus, the message can be automatically generated in response to the above processing that requests approval from the healthcare provider for the adjustment in the agent. In response to the healthcare provider approving the adjustment, a response from the healthcare provider can be received by the system and the adjustment can be made. This provides for at least some level of review by the healthcare provider.

In one or more implementations, the controller (e.g., the one or more processors 116 of FIG. 1, or the controller 208 of FIG. 2) can further instruct the user 101 on how to implement the adjustment to the delivery device 214 via one or more visual instructions presented on a display 304 of, for example, the respiratory treatment apparatus 102. The instructions can guide the user 101 on how to properly make manual adjustments so that the correct adjustment is made to the delivery device 214. The instructions can be provided in the case where the required adjustment cannot be performed automatically. For example, in one or more embodiments, the adjustment can be changing the agent to a different agent, such as changing cartridges of medications. The instructions can provide the various names of the medications, the cartridges associated with the medications, and instructions on changing out the different cartridges of the medications.

Figure 9:
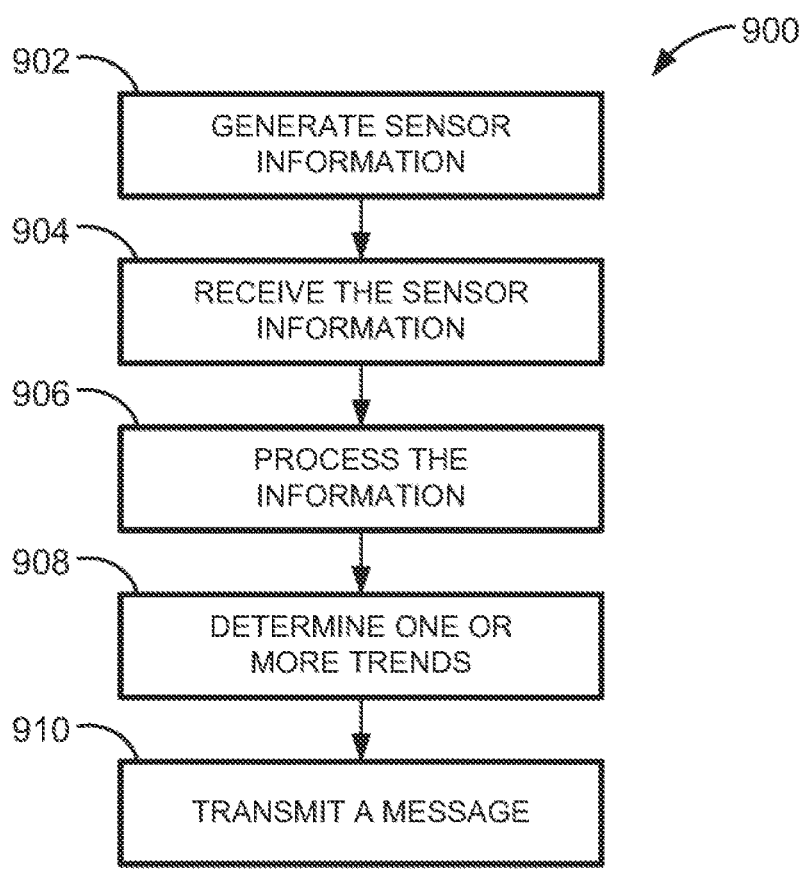
FIG. 9 is a flow diagram of a process for adjusting dosage of an agent, according to one embodiment of the present disclosure.

FIG. 9 illustrates a specific example of a process 900 for requesting approval for adjusting a dosage of an agent. The process 900 can be performed by implementing one or more of the elements of the system 100 in FIG. 1. The process 900 is similar to the process 800 discussed above in FIG. 9. Thus, elements discussed above for the process 800 also apply to the process 900, unless otherwise provided.

First (902), a sensor (or at least one sensor) that is positioned in an exhalation path of the user, and configured to detect at least one analyte in the exhaled breath of the user, generates information on the exhaled breath, similar to step 802 discussed above.

Next (904), a controller (e.g., the one or more processors 116 of FIG. 1, or the controller 208 of FIG. 2) receives the information generated by the sensor 108 based on the exhaled breath of the user. Similar to the generation of the information in process 800, the information can be transmitted by the sensor 108 to the controller continuously, periodically, or on demand.

Next (906), the one or more processors 116 process the information to determine the presence, the concentration, or a combination thereof of the at least one analyte in the exhaled breath, similar to step 806 discussed above.

Next (908), the controller (e.g., the one or more processors 116 of FIG. 1, or the controller 208 of FIG. 2) determines one or more trends in the presence, the concentration, or a combination thereof. In one or more implementations, the trends can be based on whether the presence of the analyte has become more or less prevalent. In one or more implementations, the trends can be based on an increase or a decrease in the concentration of the analyte. The trends can be determined based on using one or more algorithms, such as simple regression analysis to complex machine learning.

Next (910), the controller (e.g., the one or more processors 116 of FIG. 1, or the controller 208 of FIG. 2) causes a transmission of a message to a remote system 110 for notifying a requirement of an adjustment of a dosage of the agent for the user based, at least in part, on the one or more trends. The remote system 110 can be associated with a healthcare provider associated with the user. The prevalence of the analyte may indicate that a response is required, and the response can be an adjustment to a delivery device 214. However, the adjustment to the delivery device 214 may require approval of a healthcare provider to implement. In some implementations, the adjustment can be causing the delivery device 214 to begin delivering an agent, such as in the case where the agent was not being previously delivered.

In one or more implementations, the controller can determine whether the one or more trends satisfy at least one threshold, and further cause the transmission of the message based on satisfaction of the at least one threshold. In one or more implementations, the at least one threshold can be based, at least in part, on crowd-sourced information generated based on exhaled breath of a plurality of additional users. The threshold can be based on other users showing a similar trend and requiring similar adjustments to the delivery device.

In one or more implementations, the controller can compare the concentration of the at least one analyte to one or more physiological parameters of the user. In response, the controller can determine the adjustment of the dosage based, at least in part, on the comparison.

In one or more implementations, prior to step 910, the controller (e.g., the one or more processors 116 of FIG. 1, or the controller 208 of FIG. 2) can determine a predicted response by the user 101 to an initial adjustment of the dosage of the agent. Thereafter, the one or more processors 116 can compare the predicted response to one or more actual responses by one or more additional users to the initial adjustment. Thereafter, the one or more processors 116 can modify the initial adjustment of the dosage of the agent based on the comparison of the predicted response to the one or more actual responses to generate the adjustment of the dosage of the agent included in the message to the remote system.

The same response can occur based on a trend in the concentration of an analyte. Prior to the concentration exceeding a threshold, the delivery device may not have been administering an agent. Once the threshold is exceeded, the delivery device may begin delivering the agent. Alternatively, the adjustment may be an increase or a decrease in the amount of the agent that is being delivered. In one or more implementations, a series of presence and/or concentration determinations can occur with determinations of the concentrations. The processing can include determining a trend in the concentration from the multiple determined concentrations. A response can then be based on the determined trend. Rather than a single concentration being compared to a single threshold, a trend of the concentrations can be compared with predetermined or threshold trends. The predetermined trends indicate the potential for a concentration of the analyte to exceed a threshold, before exceeding the threshold. Accordingly, satisfaction of a determined trend with a predetermined or threshold trend can indicate that immediate action is needed prior to the concentration of the analyte meeting a threshold. This can provide for additional response time prior to the concentration of the analyte reaching a dangerous level.

For example, consumption of a large amount of a drug in a short amount of time may not immediately indicate the amount of the drug consumed. This may be a result of the inherent delay in the body metabolizing the drug. Thus, a single determination of the presence of an analyte related to the drug (or the analyte as the drug itself) may not indicate the severity of the situation. However, a trend occurs as the body metabolizes the drug and the concentration of the analyte in the breath begins to rise rapidly. Accordingly, a series of presence determinations with concentrations may reveal a trend that satisfies a predetermined or threshold trend. The satisfaction indicates that the user 101 requires a medical response to prevent injury or death despite none of the concentrations separately indicating concern (i.e., separately not satisfying a threshold).

Figure 10:
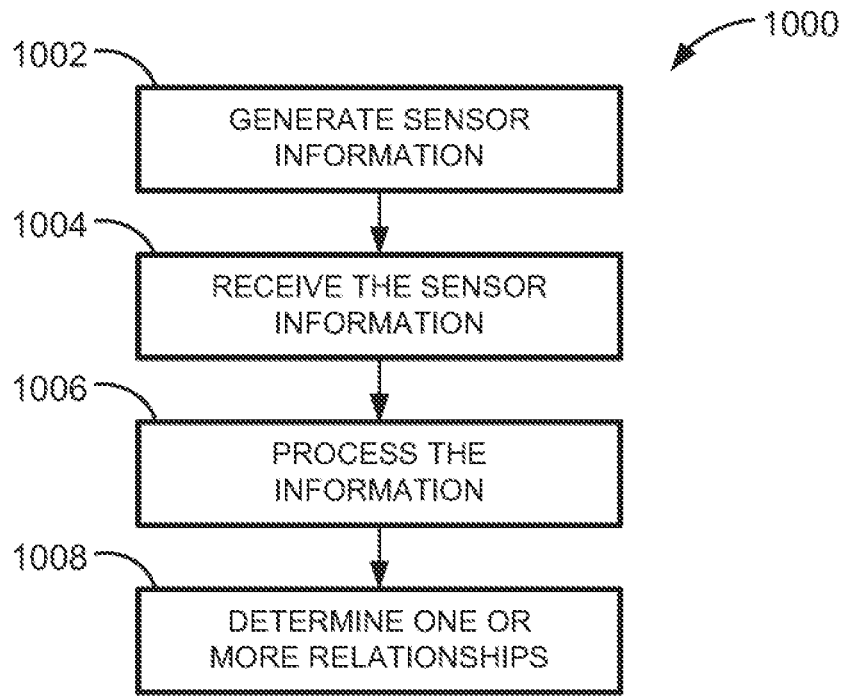
FIG. 10 is a flow diagram of a process for acquiring physiological information of a user, according to one embodiment of the present disclosure.

FIG. 10 illustrates an example of a process 1000 for acquiring physiological information of a user. The process 1000 can be performed by implementing one or more of the elements of the system 100 in FIG. 1.

First (1002), a sensor (or at least one sensor) that is positioned in an exhalation path of the user, and configured to detect at least one analyte in the exhaled breath of the user, generates information on the exhaled breath. The at least one sensor is configured to detect at least one analyte in the exhaled breath of the user over multiple discrete measurements during multiple discrete sessions.

Next (1004), the controller (e.g., the one or more processors 116 of FIG. 1, or the controller 208 of FIG. 2) receives, from the at least one sensor, information generated based on the multiple discrete measurements during the multiple discrete sessions of the at least one sensor detecting the at least one analyte in the exhaled breath of the user.

Next (1006), the controller (e.g., the one or more processors 116 of FIG. 1, or the controller 208 of FIG. 2) processes the information to determine a presence, a concentration, or a combination thereof of the at least one analyte in the exhaled breath across the multiple discrete measurements, the multiple discrete sessions, or a combination thereof.

Next (1008), the controller (e.g., the one or more processors 116 of FIG. 1, or the controller 208 of FIG. 2) determines one or more relationships between the presence, the concentration, or a combination thereof of the at least one analyte to one or more physiological parameters, one or more pharmacological parameters, or a combination thereof associated with the user across the multiple discrete measurements, the multiple discrete sessions, or a combination thereof. In one or more implementations, the one or more relationships provide for the ability to measure a user's metabolic rate for a given compound and/or predict a user's metabolic rate for a given compound based similarities between the user and other users with similar characteristics. The analytes may be related to medication, such as for therapeutic use, or various other chemicals that a user can ingest, such as for recreational use. The present technology can use one or more algorithms, such as simple regression analysis to complex machine learning, to determine the above insights for the individual and/or for whole populations.

In one or more implementations, the controller (e.g., the one or more processors 116 of FIG. 1, or the controller 208 of FIG. 2) communicate the one or more relationships to the remote system 110 (FIG. 1). The one or more processors 116 can determine the one or more relationships based on one or more machine learning algorithms.

Figure 11:
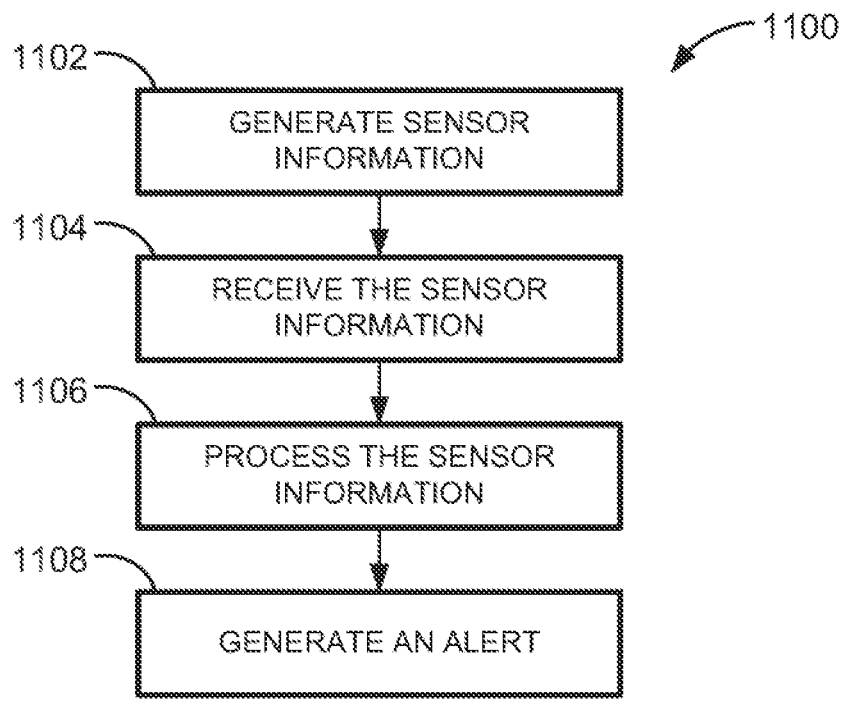
FIG. 11 is a flow diagram of a process for alerting a user of a potential for a drug interaction, according to one embodiment of the present disclosure.

FIG. 11 illustrates an example of a process 1100 for alerting a user to the potential for a drug interaction. The process 1100 can be performed by implementing one or more of the elements of the system 100 in FIG. 1.

Initially (1102), a sensor (e.g., sensor 108 of FIG. 1) that is positioned in an exhalation path of the user (e.g., user 101 of FIG. 1) that is configured to detect at least two analytes in the exhaled breath of the user. The sensor is configured to detect at least two analytes so that it can detect one analyte associated with one medication and another analyte associated with another medication. The sensor is further configured to generate information based on the exhaled breath. The information can indicate the presence or absence of the at least two analytes in the breath, such as the presence of the first analyte associated with a first medication and a second analyte associated with a second medication. The sensor can generate the information continuously, periodically, or on demand. For example, the sensor can generate the information multiple times during each breath of multiple continuous breaths, or once for each breath of the multiple continuous breaths. Alternatively, the sensor can generate the information periodically, such as once every minute, once every hour, once a night, etc. Alternatively, the sensor can generate the information upon receiving a request (e.g., from the user or from a remote system (e.g., remote system 110 of FIG. 1), etc.). The request can indicate the number and time for generating the information based on the exhaled breath, such as for each exhaled breath, once a specified number of breaths, etc.

As described above, the sensor can be a single sensor that can detect multiple different analytes. However, in one or more implementations, the sensor can instead be two different sensors. The two different sensors may be two different discrete sensors or two different sensors on the same sensor body. Each sensor can be configured to detect a different analyte. The two sensors can be located at approximately in the same location, such as both within the tube 204 or both on the user interface 106, or at different locations, such as one within the tube 204 and one on the user interface 106.

Next (1104), a controller (e.g., the one or more processors 116 of FIG. 1, or the controller 208 of FIG. 2) receives information generated by the sensor based on the exhaled breath of the user. Similar to the generation of the information, transmission of the information by the sensor to the controller can be continuous, periodic, or on demand. In one or more implementations, the information can include data only related to the presence of the at least two analytes. Alternatively, in one or more implementations, the information can include other information, such as demographic data, profile data, sensor type, and other types of data related to the at least two analytes, the sensor, the apparatus (e.g., system 100 of FIG. 1), etc.

Next (1106), the controller (e.g., the one or more processors 116 of FIG. 1, or the controller 208 of FIG. 2) processes the information to determine a presence of a first analyte of the at least two analytes, a presence of the second analyte of the at least two analytes, or a combination thereof in the exhaled breath. With respect to determining the presence, the processing may include simply determining the value of a bit within the information that provides a binary indication of the presence of the at least two analytes, or two bits within the information for the at least two analytes. For example, the bit being 1 can indicate that the at least two analytes were present in the exhaled breath, and the bit being 0 can indicate that at least one of the two analytes were not present in the exhaled breath. Alternatively, the two bits both being 1 can indicate that the at least two analytes were present in the exhaled breath, the two bits both being 0 can indicate that the at least two analytes were not present in the exhaled breath, and the two bits being 1 and 0 can indicate that one analyte was present in the exhaled breath and one analyte was not present in the exhaled breath. Thus, the information may contain multiple different formats for providing binary indications for multiple different analytes depending on the functionality of the sensor.

In one or more implementations, the controller can be configured to execute the machine-readable instructions to process the information to determine a concentration of the first analyte, a concentration of the second analyte, or a combination thereof in the exhaled breath upon determining the presence of the first analyte and the presence of the second analyte in the exhaled breath. The concentrations of the first and second analytes may be used to determine whether there is a possible drug interaction, or a severity of the possible drug interaction.

Next (1108), the controller (e.g., the one or more processors 116 of FIG. 1, or the controller 208 of FIG. 2) generates an alert for the potential of a drug interaction upon determining the presence of the first analyte and the presence of the second analyte in the exhaled breath. The presence of both the first analyte and the second analyte indicate the presence, or likelihood of the presence, of the two medications associated with the first and second analytes. Further, the two medications are associated with a drug interaction, such as a negative drug interaction that can cause adverse health conditions. Thus, it is important to alert the user of the potential for the drug interaction so that the user can take an appropriate response to the potential.

In implementations where the controller determined the concentrations of the first and second analytes, the controller can be configured to first execute the machine-readable instructions to compare the concentration of the first analyte, the concentration of the second analyte, or a combination thereof to one or more thresholds and generate the alert for the potential of the drug interaction based on the comparison. Comparison of the concentrations to one or more thresholds can indicate whether a potential for the drug interaction exists despite both analytes being detected. For example, the presence of one or both of the first and second analytes may be detected, but the concentrations may be detected at such low levels that no potential for the drug interaction exists. The system may then not generate the alert despite both analytes being present.

In one or more implementations, the alert may be generated if one of the concentrations of one of the analytes satisfies the threshold but not the other. This may be done as a precautionary measure. For example, the concentration determination for one of the analytes may be incorrect. If the concentration of one analyte satisfies the threshold, the alert can still be generated in case the concentration determination for the other analyte is incorrect.

In one or more implementations, high concentrations of the first and second analytes may indicate a potential for a drug interaction. However, in one or more alternative implementations, low concentrations of the first and second analytes may indicate a potential for a drug interaction, or a low and a high concentration for respective analytes may indicate a drug interaction. For example, medication taken by the user may result in a lower concertation of an analyte, such as where the purpose of the medication is to lower a physiological parameter of the user that is associated with the analyte. Thus, in one or more implementations, the concentrations of the first and/or second analytes satisfying the threshold(s) may be the concentrations being lower than the thresholds, or may be higher than the thresholds, or a combination of one of the concentrations being higher than a threshold and one of the concentrations being lower than a threshold.

In one or more implementations, each analyte can have a different threshold, or both analytes may be the same threshold. For example, the threshold may be a concentration that is independent of the analyte. In such cases, as examples, the threshold may be 1 milligram per liter (mg/L), 10 parts per million, etc. no matter what the two analytes are. In the alternative, the threshold may be a concentration that is dependent on the analyte and the thresholds may be different for the two analytes.

Figure 12:
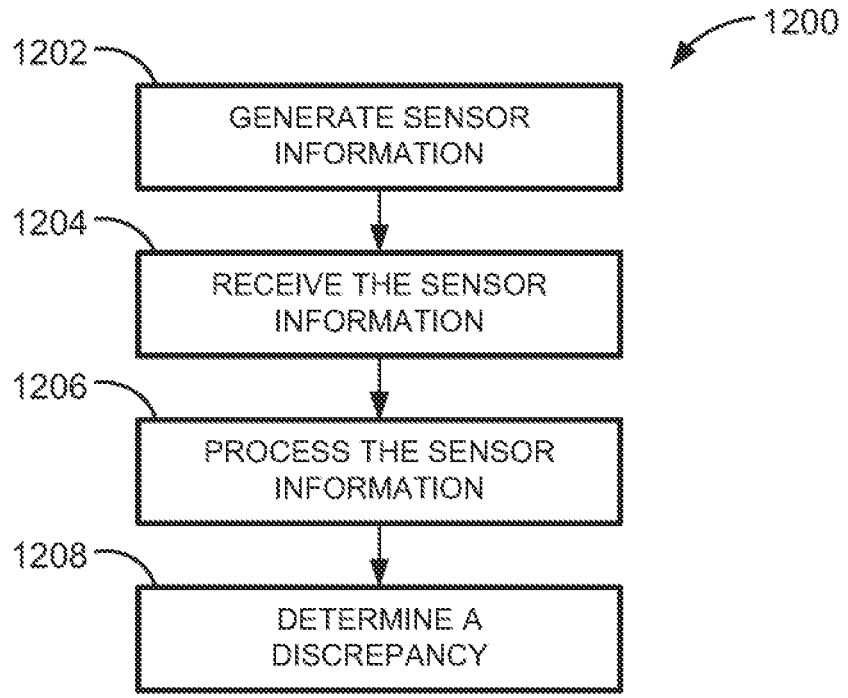
FIG. 12 is a flow diagram of a process for verifying one or more medications taken by a user, according to one embodiment of the present disclosure.

FIG. 12 illustrates an example of a process 1200 for verifying one or more medications taken by a user. The process 1200 can be performed by implementing one or more of the elements of the system 100 in FIG. 1.

First (1202), the sensor (e.g., sensor 108 of FIG. 1) that is positioned in an exhalation path of the user (e.g., user 101 of FIG. 1) that is configured to detect one or more analytes in the exhaled breath of the user 101 generates information on the exhaled breath. In one or more implementations, a single sensor can be configured to detect multiple different analytes. Alternatively, in one or more embodiments, there can be multiple sensors. Each sensor can be configured to detect a single analyte, or multiple sensors can be configured to detect multiple analytes. Each analyte can be detected by a single sensor, or there can be redundancy such that each analyte can be detected by multiple sensors.

Next (1204), a controller (e.g., the one or more processors 116 of FIG. 1, or the controller 208 of FIG. 2) receives information generated by the sensor based on the exhaled breath of the user. Similar to the generation of the information, transmission of the information by the sensor to the controller can be continuous, periodic, or on demand. In one or more implementations, the information can include data only related to the presence of the one or more analytes. Alternatively, in one or more implementations, the information can include other information, such as demographic data, profile data, sensor type, medication information, and other types of data.

Next (1206), the controller (e.g., the one or more processors 116 of FIG. 1, or the controller 208 of FIG. 2) processes the information to determine which of the one or more analytes are present in the exhaled breath. The processing may include simply determining the value of bits within the information that provide binary indications of the presence of the one or more analytes. The processing can be similar to the processing discussed above at 1106 and can be for one or medications.

Next (1208), the controller (e.g., the one or more processors 116 of FIG. 1, or the controller 208 of FIG. 2) determines a discrepancy in one or more medications taken by the user based on a discrepancy between the one or more analytes present in the exhaled breath and one or more analytes associated with the one or more medications. In one or more implementations, a discrepancy occurs if the one or more analytes present in the exhaled breath do not match the one or more analytes associated with the one or more medications taken by the user. In other words, for each medication taken by a user, an analyte is expected to be in the exhaled breath of the user. If the analyte is not in the exhaled breath of the user, a discrepancy exists.

In one or more implementations, prior to the determination of the discrepancy, the controller determines the one or more medications taken by the user. In one or more implementations, the controller can determine the one or more medications by accessing electronic medical records associated with the user listing the one or more medications.

In one or more implementations, the controller can determine the one or more medications by processing one or more images. In particular, the controller can be configured to receive one or more images of the one or more medications taken by the user, one or more containers of the one or more medications, or a combination thereof. The controller further can be configured to process the one or more images to determine the one or more medications. The processing can be based, at least in part, on one or more colors of the one or more medications, one or more indicia on the one or more medications, one or more shapes of the one or more medications, one or more indicia on the one or more containers, or a combination. For example, the controller can determine that the medication in the image is a specific color associated with a specific medication. Alternatively, or in addition, the controller can determine the medication in the image based on a specific indicia associated with the medication being on the medication in the image. Alternatively, or in addition, the controller can determine the medication in the image based on a specific indicia associated with the medication being on the container of the medication in the image. In one or more implementations, the indicia can be any character (e.g., letters and/or numbers) or any string of characters (e.g., words or non-words).

In one or more implementations, the controller can be configured to determine the one or more medications taken by the user by determining a presence of the one or more analytes associated with the one or more medications in exhaled breath of the user for a predefined number of samplings over a period of time. More specifically, prior to verifying one or more medications taken by the user, the controller can learn the one or medications that the user takes by analyzing the one or more analytes that are in the exhaled breath of the user that are also associated with the one or more medications. The learning can occur over a period of time and over a number of samples. Alternatively, the learning can occur over a period of time that is independent of the number of samples, or over a number of samples that is independent of a period of time. The controller learns the one or more medications by determining that the one or more analytes associated with the one or more medications are in the exhaled breath.

In one or more implementations, the controller can determine that a user is taking a medication based on the associated analyte being in the exhaled breath of the user for at least 50% of the samples over the period of time, over the number of samples, or a combination thereof. Alternatively, the controller can determine that a user is taking a medication based on the associated analyte being in the exhaled breath for at least 60%, or at least 70%, or at least 80%, or at least 90%, or 100% of the samples over the period of time, the number of samples, or a combination thereof.

As described above, the discrepancy between the one or more analytes present in the exhaled breath and the one or more analytes associated with the one or more medications is a lack of at least one analyte of the one or more analytes present in the exhaled breath. Alternatively, the discrepancy between the one or more analytes present in the exhaled breath and the one or more analytes associated with the one or more medications can be a presence of at least one analyte of the one or more analytes in the exhaled breath. For example, a medication that the user is supposed to take may prevent an analyte from being present in the exhaled breath. If the user stops taking the medicine, the analyte may subsequently appear in the exhaled breath. The presence of the analyte in the exhaled breath consequently indicates the discrepancy in the one or more medications.

In one or more implementations, the controller can be configured to execute the machine readable instructions to provide an alert to a third party regarding the discrepancy after a predefined number of samplings associated with the discrepancy. The alert can be directed to the user or to a third party associated with the user, such as any guardian or healthcare provider associated with the user.

Figure 13:
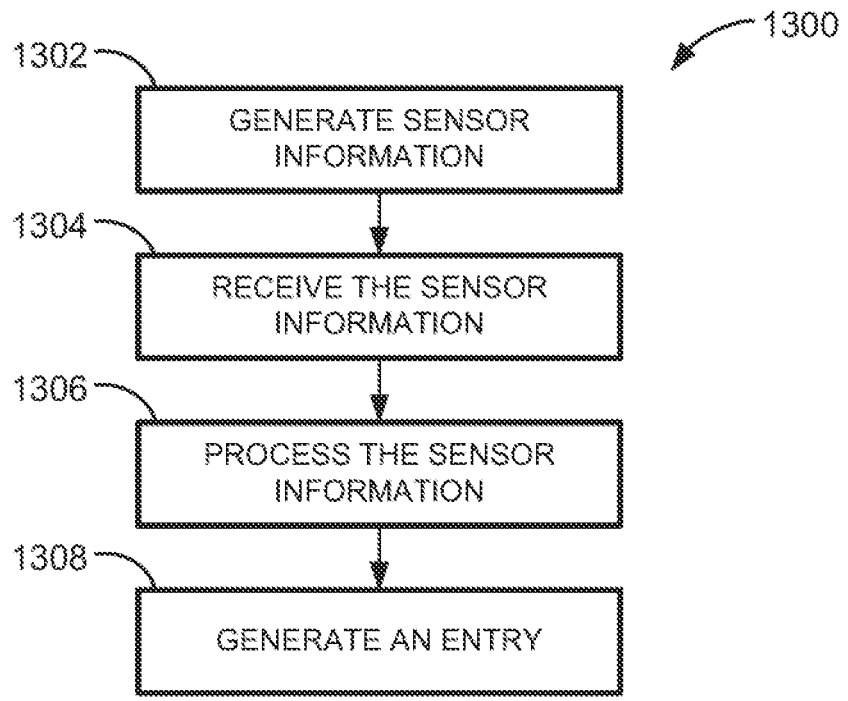
FIG. 13 is a flow diagram of a process for managing a medication regime of a user, according to one embodiment of the present disclosure.

FIG. 13 illustrates an example of a process 1300 for managing a medication regime of a user. The process 1100 can be performed by implementing one or more of the elements of the system 100 in FIG. 1.

First (1302), a sensor (e.g., sensor 108 of FIG. 1) that is positioned in an exhalation path of the user (e.g., user 101 of FIG. 1) that is configured to detect at least one analyte in the exhaled breath of the user 101 generates information on the exhaled breath. The information can indicate the presence or absence of the analyte in the breath, the concentration of the analyte, or a combination thereof. The sensor can generate the information continuously, periodically, or on demand. For example, the sensor can generate the information multiple times during each breath of multiple continuous breaths, or once for each breath of the multiple continuous breaths. Alternatively, the sensor can generate the information periodically, such as once every minute, once every hour, once a night, etc. Alternatively, the sensor can generate the information upon receiving a request (e.g., from the user or from the remote system, etc.). The request can indicate the number and time for generating the information based on the exhaled breath, such as for each exhaled breath, once a specified number of breaths, etc.

Next (1304), a controller (e.g., the one or more processors 116 of FIG. 1, or the controller 208 of FIG. 2) receives information generated by the sensor based on the exhaled breath of the user. Similar to the generation of the information, transmission of the information by the sensor to the controller can be continuous, periodic, or on demand. In one or more implementations, the information can include data only related to the presence of the analyte. Alternatively, in one or more implementations, the information can include other information, such as demographic data, profile data, sensor type, medication type, and other types of data.

Next (1306), the controller (e.g., the one or more processors 116 of FIG. 1, or the controller 208 of FIG. 2) processes the information to determine the presence of the at least one analyte in the exhaled breath. As discussed above, the processing may include simply determining the value of a bit within the information that provides a binary indication of the presence of the analyte. For example, the bit being 1 can indicate that the analyte was present in the exhaled breath, and the bit being 0 can indicate that the analyte was not present in the exhaled breath. The information may contain multiple different bits providing binary indications for multiple different analytes depending on the functionality of the sensor.

Next (1308), the controller (e.g., the one or more processors 116 of FIG. 1, or the controller 208 of FIG. 2) generates an entry regarding the medication within a record associated with the user in response to the presence of the analyte.

In one or more implementations, the presence of the analyte in the exhaled breath confirms that the user took the medication. Thus, in response, the entry can be a confirmation in the record that the user took the medication. The record can then act as a reminder to the user that the user took the medication. The reminder can be used to prevent the user from taking a double dose of the medication, or not taking the medication in fear over taking a double dose if the user does not remember whether he or she already took the medication for the required dose.

In one or more alternative implementations, the entry can be at least one future entry in the record for reminding the user of at least one future dose of the medication. Instead of reminding the user that the user already took the medication, the record can remind the user of the need to take the medication in the future.

In one or more implementations, the entry can be multiple entries that are past, present, future, or a combination therefore. The type of entry and the timing of the entry can be based on a prescription of the medication. The prescription can indicate the quantity of each dose (e.g., number of pills, ounces of fluid, etc.), the number of times a day the user is supposed to take the medication, the number of times a week the user is supposed to take the medication, etc. In one or more embodiments, the controller can be configured to determine dosage information of the medication based on accessing electronic medical records associated with the user. Alternatively, or in addition, in one or more implementations, the controller can be configured to determine the dosage information by processing one or more images. In particular, the controller can be configured to receive one or more images of the one or more medications taken by the user, one or more containers of the one or more medications, or a combination thereof. The controller further can be configured to process the one or more images to determine the one or more medications. The processing can be based, at least in part, on one or more colors of the one or more medications, one or more indicia on the one or more medications, one or more shapes of the one or more medications, one or more indicia on the one or more containers, or a combination, as described above with respect to FIG. 12.

In one or more implementations, the record associated with the user can be a personal electronic calendar. The personal electronic calendar can be accessed by the user on a user computing device 122.

In one or more implementations, the controller can provide information on the medication to the user. The information can include, for example, other medications that have adverse interactions with the medication, dosage information for the medication, or any other information that is generally associated with a user taking the medication. The controller can access a remote system (e.g., remote system 110 of FIG. 1) after determining what medication the user is taking and access information regarding that medication on the remote system. The remote system can be associated with a pharmacy or a pharmacist associated with the user, a healthcare provider associated with the user, such as the healthcare provider that prescribed the medication, with the manufacturer of the medication, and the like. Once the controller accesses the information, the controller can provide the information to the user. The information can be provided in the apparatus (e.g., the respiratory treatment apparatus 102 of FIG. 1) or a user computing device (e.g., user computing device 122 of FIG. 1).

Figure 14:
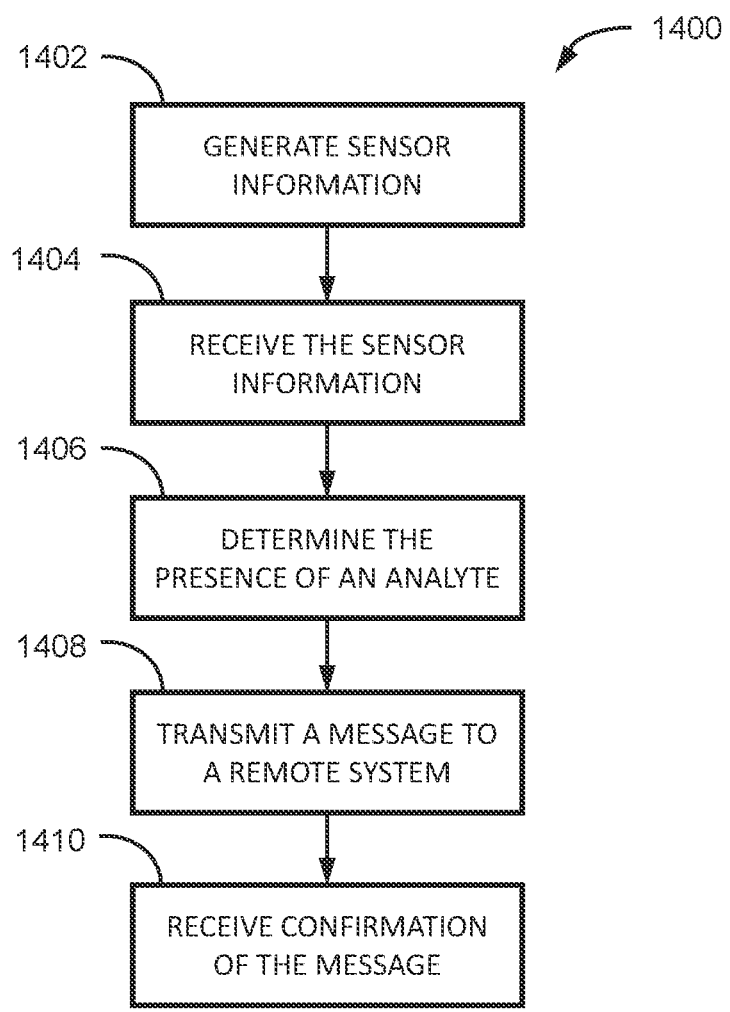
FIG. 14 is a flow diagram of a process for analyzing breath of a user, according to one embodiment of the present disclosure.

FIG. 14 illustrates an example of a process 1400 for analyzing exhaled breath of a user and transmitting a generated message regarding the exhaled breath to a remote system. The process 1400 can be performed by implementing one or more of the elements of the system 100 in FIG. 1.

First (1402), a sensor (or at least one sensor) (e.g., sensor 108 of FIG. 1) that is positioned in an exhalation path of the user (e.g., user 101 of FIG. 1) and configured to detect at least one analyte in the exhaled breath of the user generates information on the exhaled breath. The information indicates the presence or absence of the analyte in the breath. The sensor can generate the information continuously, periodically, or on demand. For example, the sensor can generate the information multiple times during each breath of multiple continuous breaths, or once for each breath of the multiple continuous breaths. Alternatively, the sensor can generate the information periodically, such as once every minute, once every hour, once a night, etc. Alternatively, the sensor can generate the information upon receiving a request (e.g., from the user or from the remote system, etc.). The request can indicate the number and time for generating the information based on the exhaled breath, such as for each exhaled breath, once a specified number of breaths, etc.

As discussed above, the sensor can be affixed to a frame, and the frame can be connected to the user so as to position the sensor along the exhalation of the path of the user. In one or more implementations, the frame can be a user interface (e.g., nasal pillows, full mask, etc.). of a continuous positive airway pressure device, as discussed above.

Next (1404), the one or more processors receive information generated by the sensor based on the exhaled breath of the user. Similar to the generation of the information, the information can be transmitted by the sensor to the one or more processors continuously, periodically, or on demand. In one or more implementations, the information can include data only related to the presence of the analyte. Alternatively, in one or more implementations, the information can include other information, such as demographic data, profile data, sensor type, and other types of data.

Next (1406), the one or more processors process the information to determine the presence of the at least one analyte in the exhaled breadth. The processing may include simply determining the value of a bit within the information that provides a binary indication of the presence of the analyte. For example, the bit being 1 can indicate that the analyte was present in the exhaled breath, and the bit being 0 can indicate that the analyte was not present in the exhaled breath. The information may contain multiple different bits providing binary indications for multiple different analytes depending on the functionality of the sensor.

In one or more implementations, the information may be more granular, such as degrees of presence. For instance, the information can indicate whether the analyte is (i) not detected, (ii) detected in a quantity typical for error or noise, (iii) detected in a quantity that indicates the presence of the analyte, or (iv) detected in such a large quantity that may indicate an error in the system, such as an error in the sensor. Examples of large quantities may include quantities that are not physically possible, such as ethanol levels that are beyond the ability for human consumption of alcohol. The granularity may be even more specific and can include both the presence of the analyte and the concentration of the analyte. The information may include the concentration directly, such that the processing entails retrieving the concentration from the information. Alternatively, the information may include the quantity of the analyte, such as the number of moles, microns, parts per million (ppm) of the analyte found in the exhaled breadth, in addition to the volume of exhaled breath that was sampled to obtain the information. In one or more implementations, the information generated from the sensor may include only the quantity, and the volume of exhaled breath may be acquired from another sensor, or from another device. For example, in the case of the user computing device being the RPT device, the volume of sampled air may be obtained from the RPT device. Thus, the processing of the information can include information from both the sensor and the user computing device, such as the RPT device.

In one or more implementations, the processing can include comparing the concentration to one or more metrics associated with the user. The metrics can be physiological metrics that, when combined with the concentration of the analyte, provide greater insight into appropriate actions to be taken. For example, comparing the concentration to the metrics allows for tailoring of the specific responses to the presence determination. Such metrics can include binary metrics, such as whether the user is a diabetic. Such metrics can be more granular, such as physiological parameters including the weight, height, body mass index, and/or age of the user.

In one or more implementations, the processing can include comparing the information from the sensor to ambient information from the environmental sensor. This comparison allows for the determination that the presence of the analyte below is from the exhaled breath of the user and not simply from the ambient air surrounding the user.

In response to the concentration of the analyte, the processing may include comparing the concentration to one or more thresholds. The thresholds correlate the concentration to predetermined actions to be taken, such as in the event of a presumption of a medical emergency based on the concentration of the analyte. Again relating back to ethanol, a concentration of ethanol that satisfies a threshold, such as above a correlated blood alcohol level, may indicate that the user requires a medical response to prevent injury or death.

In one or more implementations, a series of presence determinations can occur with determinations of the concentrations. The processing can include determining a trend in the concentration from the multiple determined concentrations. A response can then be based on the determined trend. Rather than a single concentration being compared to a single threshold, a trend of the concentrations can be compared with predetermined or threshold trends. The predetermined trends indicate the potential for a concentration of the analyte to exceed a threshold, before exceeding the threshold. Accordingly, satisfaction of a determined trend with a predetermined or threshold trend can indicate that immediate action is needed prior to the concentration of the analyte meeting a threshold. This can provide for additional response time prior to the concentration of the analyte reaching a dangerous level.

For example, consumption of a large amount of a drug in a short amount of time may not immediately indicate the amount of the drug consumed. This may be a result of the inherent delay in the body metabolizing the drug. Thus, a single determination of the presence of an analyte related to the drug (or the analyte as the drug itself) may not indicate the severity of the situation. However, a trend occurs as the body metabolizes the drug and the concentration of the analyte in the breath begins to rise rapidly. Accordingly, a series of presence determinations with concentrations may reveal a trend that satisfies a predetermined or threshold trend. The satisfaction indicates that the user 1000 requires a medical response to prevent injury or death despite none of the concentrations separately indicating concern (i.e., separately not satisfying a threshold).

Next (1408), the user computing device generates a message based on the detected presence of the analyte in the exhaled breath of the user. The message can be any type of electronic communication transmittable between computing devices. In one or more implementations, the message can be an e-mail or a communication based on a proprietary protocol. The user computing device further causes a transmission of the message to the remote system based on the determination of the presence of the analyte. The transmission of the message allows for a third party to become involved based on the presence of the analyte. Involvement of the third party can be based on a number of reasons, depending on, for example, the analyte in question, the user, and the relationship of the third party to the user, and the like.

For example, the analyte may be a prohibited substance. The substance may be prohibited for a number of reasons, such as being legally prohibited, medically prohibited, and/or nutritionally prohibited. The process allows a third party to become involved in response to the user consuming the prohibited substance.

In one or more implementations, the prohibited substance may be legally prohibited, such as a narcotic or controlled substance. The third party associated with the remote system may be first responders that can be alerted to the user consuming the narcotic. The severity or purpose of the message can vary, such as alerting police to the consumption of an illegal narcotic, or alerting paramedics to the consumption of an illegal narcotic that may cause injury or death to the user. The third party may instead be, for example, a probation officer or a parent of the user, and the message may simply indicate the consumption of the illegal narcotic but not necessarily require an immediate response or intervention. Yet, the third party still receives the message so as to alert the third party of the consumption of the illegal narcotic, which may not have occurred otherwise. For example, the user may not have otherwise informed his or her probation officer or parent of the consumption of the illegal narcotic out of guilt or the avoidance of being caught.

In one or more implementations, the prohibited substance may be something that negatively interacts with another medication or supplement that the user is consuming. Thus, while not necessarily legally prohibited, the substance may still be prohibited based on the specifics of the user. The message may be sent to a remote system of a pharmacist or other healthcare provider, or first responders, to provide an alert regarding the possible negative interaction.

In one or more implementations, the analyte may be the prohibited substance itself, or may be a metabolite that the user's body produces after consuming the prohibited substance. Indeed, in all cases, not just for prohibited substances, the analyte detected by the sensor may be a substance that the user consumed, or a metabolite of a substance that the user consumed. Alternatively, the analyte may instead be related to a physiological process of the user's body, unrelated to a substance that the user consumed. For example, nitric oxide may indicate that the user suffers from asthma, and may be unrelated to any substance that the user consumed.

In one or more implementations, the presence of the analyte may indicate a physiological condition, such as a disease or medical condition, or the onset of a disease or a medical condition. The message can alert a third-party healthcare provider of the need to follow up with the user regarding further testing required to diagnose and/or treat the disease or medical condition.

In one or more implementations, whether to transmit the message to the remote system, or the specific content of the message, may vary depending not only on the presence of the analyte but also other factors. The factors may include the concentration of the analyte satisfying a threshold, such as being above or below a set concentration. For example, although a negative interaction may exist between the prohibited substance that the user consumed and another medication or supplement, the concentration of the analyte may indicate that intervention or alerting the third party is not required. Alternatively, the concentration of the analyte may change the tone of the content of the message, such as merely indicating the presence of the analyte, to indicating immediate action is required.

In one or more implementations (1410), the user computing device may optionally receive, from the remote system, confirmation of receipt of the message. The confirmation closes the loop between the user computing device and the remote system to ensure that transmission was successful. In one or more embodiments, the confirmation may be required for documentation purposes, such as in the situation of the analyte being related to a controlled substance and the remote system being associated with first responders, the police, a probation officer, or parents of the user. In one or more implementations, the confirmation may alert the user of the transmission of the message to the third-party remote system, such to a healthcare provider, and alert the user to a scheduled appointment for follow up related to the determined presence of the analyte.

In one or more implementations, the message may include authentication to ensure that no part of the system has been modified to subvert the intended purpose. For example, the message may include an encryption key that can be decrypted by the remote system. Decryption of the encryption key to verify the authenticity of the message assists in establishing that the detection of the presence of the analyte and the generated message have not been altered. In one or more implementations, the confirmation received by the user computing device may also be authenticated so that the user has a record of the transmission and receipt of the message at the remote system. Moreover, the authentication of the confirmation ensures to the user that the confirmation receipt has not been altered.

Figure 15:
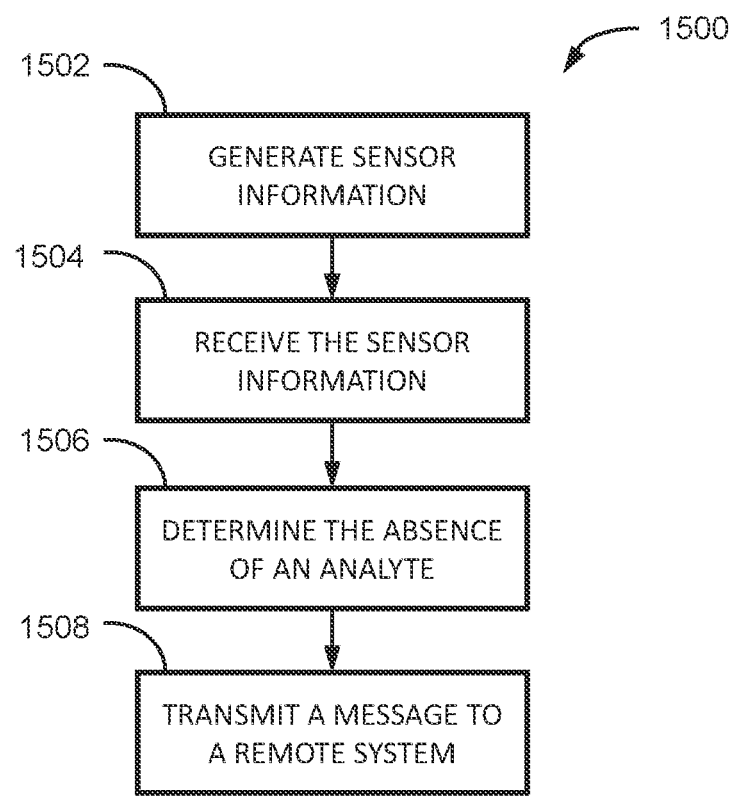
FIG. 15 is a flow diagram of another process for analyzing breath of a user, according to one embodiment of the present disclosure.

FIG. 15 illustrates an example of a process 1500 for analyzing exhaled breath of a user. The process 1500 can be performed by implementing one or more of the elements of the system 100 in FIG. 1. The process 1500 is similar to the process 1400 discussed above in FIG. 14. Thus, elements discussed above for the process 1400 also apply to the process 1500, unless otherwise provided.

First (1502), a sensor (or at least one sensor) that is positioned in an exhalation path of the user, and configured to detect at least one analyte in the exhaled breath of the user, generates information on the exhaled breath.

Next (1504), the one or more processors receive information generated by the sensor based on the exhaled breath of the user. Similar to the generation of the information in process, the information can be transmitted by the sensor to the one or more processors continuously, periodically, or on demand.

Next (1506), the one or more processors process the information to determine the absence of the at least one analyte in the exhaled breadth. Thus, the focus of the process the analyte being not present in the exhaled breath, as opposed to the focus of the process of the analyte being present in the exhaled breath. Because the focus of the process is on the absence of the analyte, in one or more implementations the information generated by the sensor can merely indicate the absence of the analyte. Alternatively, the information may be more granular and/or can include additional information. The additional information can include, for example, the time period during which the analyte was not present. The analyte may be not present during the entire time period, or may be not present on average during the entire time period, such as to account for noise or error in the sensor.

In response to the determination that the analyte is absent (1508), the one or more processors cause a transmission of a message to the remote system via the communication interface based on the determination of the absence of the analyte. The content of the message can vary depending on the analyte in question. In the case where the analyte is a controlled substance, or a metabolite of a controlled substance, the content of the message can indicate that the user has complied with a requirement. The requirement may be, for example, compliance with a mandate that the user has his or her breath sampled to determine whether the user has consumed a controlled substance. The mandate can be applied by, for example, a court order. Thus, the absence of the analyte indicates compliance of the court order.

Alternatively, in one or more implementations, the absence of the analyte indicates defiance, such as defiance of medical or nutritional regime. The user may be on a medical or nutritional regime as defined by a healthcare provider or a nutritionist, respectively, and the absence of the analyte indicates the defiance of the regime(s). For example, the user may have forgotten or decided to not take a prescription medication. The absence of the analyte in the user's exhaled breath indicates the absence of the medication in the user's system. The message can alert a healthcare provider associated with the user that the user did not take his or her medication.

In another example, the user may have forgotten or refused to take a supplement. For example, the analyte can be a vitamin or a metabolite of the vitamin. The absence of the analyte in the user's exhaled breath indicates the absence of the medication in the user's system. The message can alert a healthcare provider associated with the user that the user did not take his or her supplement.

In one or more implementations, the system can determine what vitamins or there supplements the user is missing based on the analysis if the user's breadth. The message can be sent to a nutritionist to inform the nutritionist what vitamins and/or supplements the user needs to take for establishing appropriate levels in the user.

In the foregoing description and in the accompanying drawings, specific terminology and symbols are set forth to provide a thorough understanding of the present technology. In some instances, the terminology and symbols may imply specific details that are not required to practice the technology. For example, although process steps in the assessment methodologies have been described or illustrated in the figures in an order, such an ordering may not be required. Those skilled in the art will recognize that such ordering may be modified and/or aspects thereof may be conducted in parallel and/or omitted.

Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

What is claimed is:

1. A method for adjusting dosage of an agent comprising:
receiving, from at least one sensor positioned in an exhalation path of a user and configured to detect analytes in exhaled breath of the user, information generated based on the exhaled breath of the user;
processing the information to determine a concentration of a first analyte and an absence of a second analyte in the exhaled breath;
determining an adjustment to a delivery device configured to deliver the agent to the user based, at least in part, on the concentration of the first analyte,
wherein the information generated based on the exhaled breath of the user is from multiple discrete measurements during multiple discrete sessions of the at least one sensor detecting the analytes in the exhaled breath of the user;
providing one or more visual instructions on a display that instruct the user on how to operate the delivery device to implement the determined adjustment;
determining one or more medications taken by the user by accessing electronic medical records at a remote system associated with the user listing the one or more medications; and
determining a discrepancy in the one or more medications taken by the user based on the absence of the second analyte and one or more analytes associated with the one or more medications;
causing a transmission of a first message to the remote system based on the determination of the discrepancy in the one or more medications;
receiving, from the remote system, a confirmation receipt for the first message; and verifying authenticity of the confirmation receipt based, at least in part, on a key transmitted with the confirmation receipt.

2. The method of claim 1, further comprising:
comparing the information to crowd-sourced information generated based on analysis of exhaled breath of a plurality of additional users being delivered the agent,
wherein the determining of the adjustment to the delivery device is based, at least in part, on the comparison.

3. The method of claim 1, further comprising:
determining at least one trend in the information across the multiple discrete sessions,
wherein the determining of the adjustment to the delivery device based, at least in part, on the at least one trend.

4. The method of claim 1, wherein the adjustment is based on a dosage amount, a dosage frequency, or a combination thereof of the agent.

5. The method of claim 1, further comprising causing a transmission of a second message that requests authorization for making the adjustment to the remote system.

6. The method of claim 5, wherein the remote system is associated with a healthcare provider associated with the user.

7. The method of claim 1, wherein the at least one analyte is a metabolite of the agent.

8. The method of claim 1, further comprising:
processing the information to determine a concentration of a third analyte in the exhaled breath;
comparing the concentration of the first analyte and the concentration of the third analyte to respective thresholds; and
generating an alert for a potential of a drug interaction based on the presence of the first analyte, the presence of the third analyte, and the comparison.

9. The method of claim 1, wherein the at least one sensor is positioned on a patient interface of a positive airway pressure device, and the at least one analyte is unrelated to respiratory function of the user.

10. The method of claim 1, further comprising:
determining a predicted response by the user to an initial adjustment of the dosage of the agent;
comparing the predicted response to one or more actual responses by one or more additional users to the initial adjustment; and
modifying the initial adjustment of the dosage of the agent based on the comparison of the predicted response to the one or more actual responses for the determining of the adjustment to the delivery device.

11. The method of claim 1, wherein the key transmitted with the confirmation receipt is encrypted, the method further comprising:
establishing that the confirmation receipt was not altered based, at least in part, on decrypting the encrypted key transmitted with the confirmation.

12. A system for adjusting dosage of an agent comprising:
at least one sensor positioned in an exhalation path of a user, the at least one sensor configured to detect analytes in exhaled breath of the user;
a display configured to present images to the user;
memory containing machine-readable instructions; and
a control system having one or more processors in communication with the memory, the control system configured to execute the machine-readable instructions to:
receive, from the at least one sensor, information generated based on the exhaled breath of the user;
process the information to determine a concentration of a first analyte and an absence of a second analyte in the exhaled breath;
determine an adjustment to a delivery device configured to deliver the agent to the user based, at least in part, on the concentration of the first analyte,
wherein the information generated based on the exhaled breath of the user is from multiple discrete measurements during multiple discrete sessions of the at least one sensor detecting the analytes in the exhaled breath of the user;
provide one or more visual instructions on a display that instruct the user on how to operate the delivery device to implement the determined adjustment;
determining one or more medications taken by the user by accessing electronic medical records at a remote system associated with the user listing the one or more medications; and
determining a discrepancy in the one or more medications taken by the user based on the absence of the second analyte and one or more analytes associated with the one or more medications;
causing a transmission of a first message to the remote system based on the determination of the discrepancy in the one or more medications;
receiving, from the remote system, confirmation of receipt of the first message; and
verifying authenticity of the confirmation based, at least in part, on a key transmitted with the confirmation.

13. The system of claim 12, wherein the control system is configured to execute the machine-readable instructions to compare the information to crowd-sourced information generated based on analysis of exhaled breath of a plurality of additional users being delivered the agent, and the adjustment to the delivery device is based, at least in part, on the comparison.

14. The system of claim 12, wherein the control system is configured to execute the machine-readable instructions to further determine at least one trend in the information across the multiple discrete sessions, and determine the adjustment to the delivery device based, at least in part, on the at least one trend.

15. The system of claim 12, wherein the adjustment is based on a dosage amount, a dosage frequency, or a combination thereof of the agent.

16. The system of claim 12, further comprising:
a communication interface configured to communicate with the remote system,
wherein the control system is configured to execute the machine-readable instructions to further cause, via the communication interface, a transmission of a second message that requests authorization for making the adjustment to the remote system.

17. The system of claim 16, wherein the remote system is associated with a healthcare provider associated with the user.

18. The system of claim 12, wherein the at least one analyte is a metabolite of the agent.

19. The system of claim 12, wherein the at least one analyte is the agent after being metabolized by the user.

20. The system of claim 12, wherein the at least one sensor is positioned on a patient interface of a positive airway pressure device, and the at least one analyte is unrelated to respiratory function of the user.

* * * * *